(12) United States Patent
Leontis

(10) Patent No.: US 7,910,713 B2
(45) Date of Patent: *Mar. 22, 2011

(54) RNA COMPLEXES, METHODS OF THEIR PRODUCTION

(75) Inventor: Neocles Leontis, Bowling Green, OH (US)

(73) Assignee: Bowling Green State University, Bowling Green, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/587,727

(22) Filed: Oct. 13, 2009

(65) Prior Publication Data

US 2010/0036105 A1 Feb. 11, 2010

Related U.S. Application Data

(63) Continuation of application No. 11/497,125, filed on Aug. 1, 2006, now Pat. No. 7,601,824.

(60) Provisional application No. 60/705,041, filed on Aug. 3, 2005.

(51) Int. Cl.
   *C07H 23/02* (2006.01)

(52) U.S. Cl. .................. 536/23.1; 977/704; 977/773
(58) Field of Classification Search .................. None
See application file for complete search history.

(56) References Cited

U.S. PATENT DOCUMENTS 7,553,945 B2 * 6/2009 Leontis .................. 536/23.1
7,601,824 B2 * 10/2009 Leontis .................. 536/23.1

* cited by examiner

*Primary Examiner* — Richard Schnizer
(74) *Attorney, Agent, or Firm* — Roger A. Gilcrest

(57) ABSTRACT

The invention includes RNA complexes comprising at least three monomeric units of an RNA molecule, each monomeric unit comprising an RNA polymer having first and second helical domains that have respective first and second binding sites, wherein the first binding sites are adapted to binding to one another and are not adapted to bind to the second binding sites, and the second binding sites are adapted to binding to one another and are not adapted to bind to the first binding sites; such that the at least three monomeric units are adapted to self-assemble by forming pairs of cognate interactions and so as to form the RNA complex in a circular closed complex. The invention also includes derivatives of these complexes including aptamers, and analytical methods and devices using same.

11 Claims, 19 Drawing Sheets

FIG-7 (COMPARATIVE)

ific lateral stereospecific binding site interactions, such as loop-receptor interactions described herein. These complexes may be assemblies of varying size, geometry, stoichiometry and cooperativity, and may even form expandable oligomeric complexes.
RNA COMPLEXES, METHODS OF THEIR PRODUCTION

RELATED APPLICATION DATA

This application is a continuation of U.S. application Ser. No. 11/497,125, now U.S. Pat. No. 7,601,824, filed Aug. 1, 2006, which claims the priority benefit of U.S. Provisional Application Ser. No. 60/705,041 filed Aug. 3, 2005, which are hereby incorporated herein by reference in their entirety.

TECHNICAL FIELD

The present invention is in the fields of biochemistry and molecular biology, and relates to analytical methods in those fields.

BACKGROUND OF THE INVENTION

In the fields of biochemistry and molecular biology, it is often desirable to be able to prepare stable and reproducible molecular constructs that may serve as templates or reagents in analytical schemes designed to detect the presence of organic and biochemical analytes.

Living systems rely almost exclusively on supramolecular self-assembly to generate complex functional, hierarchical structures over a wide range of scales. Not surprisingly, self-assembly is increasingly being adapted as a general strategy for generating nanostructures in many fields, from physics and chemistry to biology, material science, engineering and manufacturing. A major goal of nanoscience and nanotechnology is therefore to achieve fundamental control over supramolecular self-assembly—the bottom-up organization of matter on the nano-scale. "RNA tectonics" exploits the modular character of natural RNA molecules—which can be decomposed into a large variety of RNA structural motifs—to build new nanoscopic RNA architectures that self-assemble to form nano-assemblies of desired size and shape. RNA is fully programmable and amenable to design by reverse folding.

It is desirable to be able to develop RNA as a medium for (1) exploring principles of supramolecular self-assembly and (2) achieving nano-scale molecular design and construction of complex cooperative assemblies capable of realizing diverse functions and practical applications.

There is also a need for biomolecules that can be used as stable electrophoresis markers and electron microscopy markers.

There also remains a need for RNA constructs with increased stability, and those that may be readily and reliably applied in analytical methods and devices by using conformational strategies of bind, isolate and detect target biomolecules.

SUMMARY OF THE INVENTION

The present invention begins with the manipulation of structural motifs in 3D space to create "tectoRNA" molecules programmed to self-assemble as desired. Next, the supporting 2D (secondary) structure is designed and used in turn to specify a compatible and uniquely folding nucleotide sequence.

The present invention includes tectoRNA molecules that cooperatively assemble into closed, oligomeric complexes.

The present invention also includes directional and conformation-specific self-assembling RNA complexes of various sizes.

The present invention includes closed complexes formed by H-shaped tectoRNA molecules based on 4-way junctions (4WJ) and specific lateral stereospecific binding site interactions, such as loop-receptor interactions described herein. These complexes may be assemblies of varying size, geometry, stoichiometry and cooperativity, and may even form expandable oligomeric complexes.

In general terms, the invention includes an RNA complex comprising at least three monomeric units of an RNA molecule, each monomeric unit comprising an RNA polymer having a first helical domain that comprises a first overlapping portion (referred to as a helical stacking domain) having a first and second binding site (such as, respectively, a receptor site and a loop site), the first helical domain connected to a second helical domain that comprises a second overlapping portion (or helical stacking domain) having a first and second binding site (such as, respectively, a loop site and a receptor site), wherein the first binding sites are adapted to binding to one another and are not adapted to bind to the second binding sites, and the second binding sites are adapted to binding to one another and are not adapted to bind to the first binding sites; such that the at least three monomeric units are adapted to self-assemble by respective first binding sites interacting with first binding sites of respective adjacent monomeric units, and respective second binding sites interacting with second binding sites of respective adjacent monomeric units, to form pairs of cognate interactions and so as to form the RNA complex in a circular closed complex.

The first and second binding sites may also be two loop sites or two receptor sites with respective pairs of receptor or loop sites on the monomeric unit to be bound, and equivalent variations thereof involving so-called loop and receptor interactions. Typically first and second binding sites bind to one another through non-Watson-Crick interaction. The "loops" are typically terminal loops at the end of the helical domains while the "receptors" are loop structures formed internally within the body of the helical stacking domains as shown in the Figures herein where a given loop $L_n$ interacts with a receptor $R_n$ where n is an integer used for corresponding identification.

In addition, the binding sites that may be used in accordance with the present invention may also include any structure that is capable of forming, directly or indirectly, site-specific RNA-RNA binding interactions (i.e., interactions that resist dissociation). Examples may include hairpin loops, internal loops and junction loops. These interactions may be of any type including non-Watson-Crick interaction, Watson-Crick interaction or other stereospecific non-covalent interactions. Other examples may include the use of chemical moieties (synthetic or native) attached to the RNA monomers that are likewise capable of stereospecific non-covalent interactions.

The invention also includes an RNA complex comprising at least three monomeric units of an RNA molecule, each monomeric unit comprising RNA having a first helical domain having a first receptor site and a second receptor site, the first helical domain connected to a second helical domain having a first loop site and a second loop site; such that the at least three monomeric units are adapted to self-assemble by respective first receptor sites interacting with first loop sites of respective adjacent monomeric units, and respective second receptor sites interacting with second loop sites of respective adjacent monomeric units, to form pairs of cognate interactions and so as to form the RNA complex in a circular closed complex.

The first helical domain and the second helical domain are substantially parallel, and wherein the first helical domain and the second helical domain are connected by a covalently bound bridge portion such that the first helical domain and the second helical domain are held in position with respect to one another. The first helical domain and the second helical domain typically are connected by a covalently bound bridge portion, and wherein the positions of the first receptor site, the second receptor site, the first loop site and a second loop site are maintained such that the first receptor and the second loop site are spatially compatible in only one possible orientation of the adjacent monomeric units.

It is also preferred that the positions of the binding site pairs, e.g., comprising the first receptor site, the second receptor site, the first loop site and a second loop site are maintained such that the binding site pairs are spatially compatible in only one possible orientation of the adjacent monomeric units, e.g. where the second receptor site and the first loop site align and where the second loop site and the first receptor site align. This may be accomplished by using different numbers of Watson-Crick base pairs between the binding sites on the monomer units (wherein 11 base pairs provides a rotation of 360 degrees), and/or using elements or structures that change this ratio such that the same degree of helicity may be obtained with more or fewer base pairs, such as through the use of a so-called C-loop structures occurring in natural ribosomal RNAs and described in Nucleic Acids Research 2005 33(8):2395-2409 (April 2005) and which is hereby incorporated herein by reference.

In order to have binding be permitted only in one configuration, the distances between the interacting binding sites (e.g., loops and receptors) from the cross-over point are adjusted so that they are optimal for assembly in only one conformation.

Where receptor and loop sites are used on respective helical domains, it is preferred that the first receptor site is incompatible with the second loop site, and the second receptor site being incompatible with the second receptor site.

The RNA complex of the present invention may be of any size but typically will be a trimer, tetramer, pentamer or hexamer in a circular series.

The invention also includes a method of making a self-assembled RNA complex as described herein comprising the steps: (a) placing in solution at least three monomeric units of an RNA molecule, each monomeric unit comprising RNA having a first helical domain having first and second binding site (such as, respectively, a receptor site and a loop site), the first helical domain connected to a second helical domain having a first and second binding site (such as, respectively, a loop site and a receptor site); and (b) allowing the at least three monomeric units to react such that the at least three monomeric units self-assemble by respective first binding sites interacting with first binding sites of respective adjacent monomeric units, and respective second binding sites interacting with second binding sites of respective adjacent monomeric units, to form pairs of cognate interactions and so as to form the RNA complex in a circular closed complex.

Again, the first and second binding sites may also be two loop sites or two receptor sites with respective pairs of receptor or loop sites on the monomeric unit to be bound.

RNA complexes of the present invention have stable conformations and readily determined molecular weight and size, and accordingly may be useful as electrophoresis markers, and as electron microscopy markers.

RNA Monomer Comprising Aptamer

The present invention also includes an RNA molecule as described, having a first helical domain having a first binding site and a second binding site, the first helical domain connected to a second helical domain having a first binding site and a second binding site; such that the at least three monomeric units are adapted to self-assemble by respective first binding sites interacting with first binding sites of respective adjacent monomeric units, and respective second binding sites interacting with second binding sites of respective adjacent monomeric units, to form pairs of cognate interactions and so as to form the RNA complex in a circular closed complex, at least one of the monomeric units comprising an aptamer.

RNA Complex Per Se with at Least One of the Monomers having an Aptamer

The present invention also includes directional and conformation-specific self-assembling RNA complexes of various sizes that include aptamers, and their application as platforms for improved aptamer-based biosensors.

The invention further includes an RNA complex as described otherwise herein comprising at least three monomeric units of an RNA molecule, each monomeric unit comprising RNA having a first helical domain having a first receptor site and a second receptor site, the first helical domain connected to a second helical domain having a first loop-site and a second loop site; such that the at least three monomeric units are adapted to self-assemble by respective first receptor sites interacting with first loop sites of respective adjacent monomeric units, and respective second receptor sites interacting with second loop sites of respective adjacent monomeric units, to form pairs of cognate interactions and so as to form the RNA complex in a circular closed complex, at least one of the monomeric units comprising an aptamer.

As used herein, the term "aptamer" refers to reagents generated in a selection from a combinatorial library (typically in vitro) wherein a target molecule, generally although not exclusively a small molecule such as a metabolite or a drug, or a protein or nucleic acid, is used to select from a combinatorial pool of molecules, generally although not exclusively oligonucleotides, those that are capable of binding to the target molecule. The selected reagents can be identified as primary aptamers. The term "aptamer" includes not only the primary aptamer in its original form, but also secondary aptamers derived from (i.e., created by minimizing and/or modifying) the primary aptamer. Aptamers, therefore, must behave as ligands, binding to their target molecule. Aptamers that bind small molecules have been shown to undergo conformational changes upon interactions with their cognate ligands. A reporter fluorophore introduced into an aptamer in a region known to undergo conformational change can lead to a change in fluorescence intensity or polarization after the binding event. The use of aptamers in RNA constructs is described for instance in U.S. Pat. Nos. 6,458,559 and 6,706,481 which are hereby incorporated herein by reference. The aptamer may also select for other types of target molecules, such as organic molecules such as pharmaceuticals, carbohydrate or other biomolecules. The role of the aptamer generally is to allow for a change in the conformation of the aptamer containing RNA of a helical stacking domain such that its binding sites become stereochemically better disposed to binding interaction.

The first helical domain and the second helical domain typically are substantially parallel, and are connected by a covalently bound bridge portion (i.e., by being connected covalently to form a four-way junction) such that the first helical domain and the second helical domain are held in position with respect to one another. In order to assure the desired self-assembly, the positions of the respective first binding sites and second binding sites are maintained such that the first binding sites and the second binding sites are spatially compatible in only one possible orientation of the adjacent monomeric units.

The first binding sites may also be constructed so as to be incapable of binding with the second binding sites on neighboring molecules in the complex, to best assure the desired orientation of the adjacent monomeric units.

The monomers may be designed so as to self-assemble into trimers, tetramers, pentamers, hexamers, heptamers or octamers, or even more complex closed shapes as described herein.

In another variation of the present invention, the RNA complex may comprise at least three monomeric units of an RNA molecule, each monomeric unit comprising RNA having a first helical domain having a first and second binding site, the first helical domain connected to a second helical domain having a first and second binding site, wherein the first binding sites are adapted to binding to one another and are not adapted to bind to the second binding sites, and the second binding sites are adapted to binding to one another and are not adapted to bind to the first binding sites; such that the at least three monomeric units are adapted to self-assemble by respective first binding sites interacting with first binding sites of respective adjacent monomeric units, and respective second binding sites interacting with second binding sites of respective adjacent monomeric units, to form pairs of cognate interactions and so as to form the RNA complex in a circular closed complex, at least one of the monomeric units comprising an aptamer.

Method of Forming an RNA Complex with at Least One of the Monomers Having an Aptamer The present invention also includes a method of making a self-assembled RNA complex comprising the steps: (a) placing in solution at least three monomeric units of an RNA molecule, each monomeric unit comprising RNA having a first helical domain having a first binding site and a second binding site, the first helical domain connected to a second helical domain having a first binding site and a second binding site, at least one of the monomeric units comprising an aptamer and a substance that interacts with the aptamer; and allowing the at least three monomeric units to react such that the three or more monomeric units self-assemble by respective first binding sites interacting with first binding sites of respective adjacent monomeric units, and respective second binding sites interacting with second binding sites of respective adjacent monomeric units, to form pairs of cognate interactions and so as to form the RNA complex in a circular closed complex.

Again, it is preferred that the first and second helical domains are substantially parallel, and wherein the first helical domain and the second helical domain are connected by a covalently bound bridge portion such that the first helical domain and the second helical domain are held in position with respect to one another; and the first binding sites and a second binding sites are maintained such that the first binding and the second binding site are spatially compatible in only one possible orientation of the adjacent monomeric units.

The present invention also included biosensors and analytical methods based on cooperative tectoRNA complexes, which may be based upon the effects of RNA self-assembly on the affinity and cooperativity of analyte binding.

Method of Determining Presence of an Analyte by Formation of an RNA Complex with at Least One of the Monomers Having an Aptamer Reacting with the Analyte The present invention also includes a method of determining the presence or absence of an analyte through the formation a self-assembled RNA complex, the method comprising the steps: (a) placing in solution at least three monomeric units of an RNA molecule, each monomeric unit comprising RNA having a first helical domain having a first and second binding site, the first helical domain connected to a second helical domain having a first and second binding site, at least one of the monomeric units comprising an aptamer adapted to react with the analyte; and (b) allowing the one or more of the monomeric units comprising an aptamer to react with the analyte, and such that the at least three monomeric units self-assemble by respective first binding sites interacting with first binding sites of respective adjacent monomeric units, and respective second binding sites interacting with second binding sites of respective adjacent monomeric units to form pairs of cognate interactions and so as to form the RNA complex in a circular closed complex; and (c) determining the presence or absence of the complex.

The presence or absence of the complex may be determined by any method, such as by a method selected from the group consisting of electrophoresis, chromatography and surface plasmon resonance.

Sensor for Determining Presence of an Analyte by Formation of an RNA Complex with at Least One of the Monomers Having an Aptamer Reacting with the Analyte The present invention also includes a sensor adapted to bind an analyte, the sensor in general terms comprising: (a) a vessel containing a solution of at least three monomeric units of an RNA molecule, each monomeric unit comprising RNA having a first helical domain having a first and second binding site, the first helical domain connected to a second helical domain having a first and second binding site, at least one of the monomeric units comprising an aptamer adapted to react with the analyte such that the at least three monomeric units are adapted to self-assemble in the presence of the analyte by respective first binding sites interacting with first binding sites of respective adjacent monomeric units, and respective second binding sites interacting with second binding sites of respective adjacent monomeric units, to form pairs of cognate interactions and so as to form an RNA complex in a circular closed complex; and means to detect the presence or absence of the complex.

The detection means may be any means adapted to detect the presence of the closed complex, such as an instrument for carrying out an analytical method selected from the group consisting of electrophoresis, chromatography and surface plasmon resonance, such as those known in the art. This detection may also be facilitated by using fluorescent markers on one of the RNA monomers, as described herein to render the monomers or the complexes they form detectable by fluorescence-based techniques and instrumentation.

Method of Determining Presence of Two or More Analytes by Formation of an RNA Complex with at Least One of the Monomers Having an Aptamer Reacting with the Analyte Another aspect of the present invention is a method of determining the presence of at least two analytes in solution through the formation of respective self-assembled RNA complexes, the method comprising the steps: (a) placing in contact with the solution the surface of two silicon cantilevers bearing respective monomeric units of an RNA molecule of a respective first and second type, each monomeric unit comprising RNA having a first helical domain having a first and second binding site, the first helical domain connected to a second helical domain having a first and second binding site, and the monomeric unit of the first type comprising an aptamer adapted to react with the first of the two analytes, and the monomeric unit of the second type comprising an aptamer adapted to react with the second of the two analytes; (b) the solution containing additional monomeric units of an RNA molecule of a third and fourth type, each monomeric unit comprising RNA having a first helical domain having a first and second binding site, the first helical domain connected to a second helical domain having a first and second binding site, such that monomeric units of the first, third and fourth types self-assemble by respective first binding sites interacting with first binding sites of respective adjacent monomeric units, and respective second binding sites interacting with second binding sites of respective adjacent monomeric units to form pairs of cognate interactions and so as to form the RNA complex in a circular closed complex on the respective silicon cantilever surface should the first analyte be present in the solution; and such that monomeric units of the second, third and fourth types self-assemble by respective first binding sites interacting with first binding sites of respective adjacent monomeric units, and respective second binding sites interacting with second binding sites of respective adjacent monomeric units to form pairs of cognate interactions and so as to form the RNA complex in a circular closed complex on the respective silicon cantilever surface should the second analyte be present in the solution; and (c) determining the presence or absence of the complexes on the respective silicon cantilever surfaces.

Cantilever Detection Apparatus Having Cantilevers with Analyte-Specific Aptamer-Bearing Monomers The present invention also comprises an apparatus for determining the presence of a plurality of analytes in solution through the formation respective self-assembled RNA complexes, the apparatus comprising a plurality of silicon cantilevers, each having attached to its surface respective monomeric units of an RNA molecule, each monomeric unit comprising RNA having a first helical domain having a first and second binding site, the first helical domain connected to a second helical domain having a first and second binding site, and each monomeric unit comprising an aptamer adapted to react with a respective one of the plurality of analytes.

This apparatus may additionally comprise means for measuring the change in the surface characteristics of silicon cantilevers in response to the formation of an RNA complex in a circular closed complex thereupon. An example is a laser adapted to detect changes in the angle of the surface of the silicon cantilevers by detection of the reflected light from the cantilever.

RNA Monomer Comprising Fluorescent Marker and Complexes

Another variation of the present invention is an RNA molecule comprising RNA having a first helical domain having a first binding site and a second binding site, the first helical domain connected to a second helical domain having a first binding site and a second binding site, at least one of the helical domains comprising a fluorescent reporter molecule moiety. These monomers include an RNA molecule as described, having a first helical domain having a first binding site and a second binding site, the first helical domain connected to a second helical domain having a first binding site and a second binding site; such that the at least three monomeric units are adapted to self-assemble by respective first binding sites interacting with first binding sites of respective adjacent monomeric units, and respective second binding sites interacting with second binding sites of respective adjacent monomeric units, to form pairs of cognate interactions and so as to form an RNA complex in a circular closed complex, at least one of the helical domains comprising a fluorescent moiety. Examples may include fluorescein and tetramethylrhodamine (TAMRA), or various non-fluorescent quenchers.

The invention further includes an RNA complex as described otherwise herein comprising at least three monomeric units of RNA at least one of which has a helical domain comprising a fluorescent moiety.

These fluorescent variations of the RNA complexes of the present invention may be used as analytical markers, such as in analytical schemes described herein.

Still another aspect of the present invention includes methods and compositions related to the in vitro selection methods by which RNA monomers can be found that interact with RNA monomers with newly developed binding sites (i.e., loop or receptor sites of a previously unapplied nucleotide sequence). In these methods, a new binding site sequence desired to be matched is put in place of an already characterized binding site sequence in a first RNA molecule. The corresponding receptor region of another RNA molecule is then randomized to create a library of RNA molecules from which to select molecules that bind to the new site. Positive selection is then carried out by mixing the combinatorial library with the new site-bearing RNA molecule. Complexes such as trimers formed may then be separated by electrophoresis gels, while non-binding RNA candidates are eliminated. The complexes may then be selectively taken from the gel and amplified to obtain RNA molecules bearing binding sites that bind to the new binding site sequence. Both positive and negative selection is possible with this method, allowing one to obtain truly orthogonal loop-receptor pairs, for instance.

This method leads to the formation of RNA complexes wherein the binding interaction between one pair of RNA monomers is weaker than the binding interaction between the other pairs of RNA monomers. These compositions are, accordingly, useful as indicators in the subject selection method to be able to arrive at conjugate RNA monomer bearing a binding site for the new binding site.

RNA Complexes Formed in In Vitro Selection Technique and Further Orthogonal Selection Accordingly, the invention also includes a method of identifying an RNA molecule capable of forming a self-assembled RNA complexes with RNA molecules of two or more known types, the method comprising the steps: (a) placing in solution: (i) monomeric units of an RNA molecule of a respective first and second type, each monomeric unit comprising RNA having a first helical domain having a first and second binding site, the first helical domain connected to a second helical domain having a first and second binding site, such that the first and second types are adapted to bind to one another and; (ii) a plurality of monomeric units of an RNA molecule of a third type, each monomeric unit comprising RNA having a first helical domain having a first and second binding site, the first helical domain connected to a second helical domain having a first and second binding site, the first and second binding sites of the third type first helical domain adapted to bind to respective first and second binding sites of the first type first helical domain, and the first binding site of the third type second helical domain adapted to bind to respective first binding site of the second type second helical domain, and the second binding site of the third type second helical domain being randomized, such that only some of the monomeric units of an RNA molecule of the third type self-assemble with the first and second types by respective adjacent monomeric units forming pairs of cognate interactions and so as to form an RNA complex in a circular closed complex; (b) separating from the solution the RNA complex so formed; and dissociating the RNA molecule of the third type from the RNA complex so as to isolate an RNA molecule of the third type.

The method may also include the step of amplifying the RNA molecule of the third type isolated from the RNA complex.

In order to further use negative selection to obtain orthogonal binding sites, such as loop-receptor pairs, for instance, the method may further include (d) placing in solution the isolated RNA molecules of the third type with monomeric units of an RNA molecule of respective the first type and a fourth type, each monomeric unit comprising RNA having a first helical domain having a first and second binding site, the first helical domain connected to a second helical domain having a first and second binding site, such that the first and fourth types are adapted to bind to one another; (e) allowing the isolated RNA molecules of the third type to react with monomeric units of the first and fourth types, such that only some of the isolated RNA molecules of the third type self-assemble with the first and fourth types by respective adjacent monomeric units forming pairs of cognate interactions and so as to form an RNA complex in a circular closed complex; and (e separating from the solution the isolated RNA molecules of the third type that do not so self-assemble with the first and fourth types. This method may also include amplifying the isolated RNA molecules of the third type that do not so self-assemble with the first and fourth types.

Naturally, these techniques may be applied by using additional monomers of additional types (such as 5th, 6th, etc. known types), each of which has a binding site such as one of the loops) that is known and for which the binding site pair (i.e., loop-receptor motifs) have been characterized, such that any new molecules are selected so as to be orthogonal to all currently available known binding sites (i.e., loops); and in this way a mutually orthogonal "library" or "toolkit" of interacting loop-receptor motif pairs may be obtained.

For example, to ensure that the selected receptors do not bind to other sites on characterized RNA monomers in the complex (i.e., rather than the randomized site as intended), the combinatorial library is subjected to a round of negative selection to eliminate molecules that form trimer complexes when the original RNA monomer from which the "new site" RNA monomer is made (i.e., that having a known binding site sequence in place of the new site) is substituted in place of the RNA monomer containing the new binding site sequence (such as when molecule 11B is substituted for molecule 11B (NL)). This is done by running native gels and selecting molecules that do not associate with the original RNA monomer to form dimers, and that do not form trimers with the original RNA monomer from which the "new site" RNA monomer is made and the original RNA monomer from which the randomized RNA monomer is derived (e.g., molecules 11B and 11C, respectively).

The present invention helps to address one of the core aims of nanoscience, that being to design, build and analyze objects and devices with nanometer scale features. This is many times smaller than the micrometer scale of current technology, but an order of magnitude larger than the scale on which chemists traditionally have worked, and thus poses new challenges for molecular science. Supramolecular self-assembly designates "bottom-up" processes in which pre-formed, molecular components, accessible by chemical or enzymatic synthesis, associate by non-covalent interactions that exhibit sufficient binding affinity and specificity to achieve equilibrium polymerization or oligomerization, and thus offers one of the most general strategies for generating nanostructures (Whitesides & Boncheva 2002; Roco 2003).

The reversibility of non-covalent interactions allows for error-correction and adaptability during assembly and presupposes a fluid environment that provides for mobility of components so that incorrect interactions can dissociate to allow correct binding partners to find one another. Functional biological systems constructed on the nanoscale (e.g. microtubules and microfilaments, ribosomes, spliceosomes, and chromatin), exemplify these principles and inspire nanoscientists and molecular engineers (Ball 2002). The components of biological systems associate by exploiting shape complementarity, charge neutralization, hydrogen bonding and hydrophobic interactions. Self-assembly through templating is a key property of biological nanoscale systems. Base pairing in nucleic acids illustrates three features of templated self-assembly: (1) relatively high binding affinity made possible by multiple, non-covalent interactions, (2) high specificity made possible by directional H-bonding, and (3) formation of predictable 3D structure—the double helix—through strand complementarity. To overcome the limited utility of linear nucleic acids (e.g. double helical DNA or RNA) for nano-design, stable, branching motifs such as 3- or 4-way junctions are used to construct complex structures (Seeman 2003). As individual branched junctions are inherently flexible, Seeman and co-workers introduced double junction structures (Fu & Seeman 1993) and used these to create tiles to cover 2D surfaces (Winfree et al. 1998). Triple crossover (TX) motifs containing three fused double helices were prepared and applied to molecular computation (Seeman 2003). DNA has been employed to design dynamic nanomechanical devices (Mao et al. 1999; Yan et al. 2002) and even a ribosome-like DNA synthesis device (Liao & Seeman 2004). Both DNA structural transitions and branch migration have been used as the basis for the operation of DNA nanomechanical devices.

While remarkable progress has been achieved in DNA nanoscience, there are good reasons for developing RNA nanoscience. First, the presence of the 2'-hydroxyl group endows the minor groove of RNA with the capability to form a variety of tertiary interactions, including specific ones between loops and receptors (see below) making possible modes of interaction not available to DNA. Recent crystallographic achievements have made available to molecular engineers a rich treasure trove of RNA structural motifs including novel RNA-RNA interactions. Second, complex natural nanomachines such as the ribosome and splicesome are composed primarily of RNA, and RNA enzymes (ribozymes) remain the only natural exception to the "enzymes-are-polypeptides" dogma (Emilsson & Breaker 2002). RNA nanoscience draws inspiration from these complex assemblies and, contributes to a better understanding of their structures, functions and dynamics. Third, a great diversity of aptamers as well as catalytic RNA molecules have been obtained by in vitro selection (artificial evolution) methods. Natural aptamers acting as genetic regulators ("riboswitches") were recently discovered in untranslated regions of mRNAs that sense and respond to changes in the concentrations of metabolites (Winkler & Breaker 2003). Binding of the target molecule to the recognition element, usually located in the 5'-UTR of the mRNA, results in allosteric changes of the RNA secondary and tertiary structure. The structural changes modulate gene expression by various mechanisms, including transcription termination, translation initiation, or mRNA processing. The existence of a unique two-domain riboswitch that appears to cooperatively bind glycine molecules indicates that RNA molecules can be as versatile as proteins in their responses to changes in the environment. The glycine-activated riboswitch consists of two tandem glycine aptamers that respond cooperatively to glycine concentration with a Hill coefficient of 1.64 (Mandal et al. 2004). Cooperative binding by protein enzymes, receptors and gene control factors provides cells with the means to respond to small changes in ligand concentrations. The present invention allows one to construct RNA molecules tuned to respond to small changes in analyte concentration in a desired concentration range by coupling analyte binding to RNA self-assembly. RNA presents advantages as a medium for supra-molecular design, owing to its well-defined hierarchy of folding. Natural RNA molecules are 3D mosaics that are resolvable into modular motifs. The modular units can be classified geometrically and functionally. A-form double helices function as rigid struts that connect other modular structural elements, including terminal hairpin loops, internal loops ("2-way junctions"), and multi-helix or junction loops, which serve as branch points, thus making complex molecular architectures possible. Motifs can also be classified according to their functions: some serve to mediate RNA-RNA or RNA-protein interactions, others to bind small molecules or substrates, others to organize catalytic sites, and still others to provide points of flexibility (e.g. Kink-turns) or to stabilize changes in helicity (e.g. C-loops). Modularity implies independence. Thus, new architectures can be designed and constructed by reorganizing modular motifs in novel ways, just as creative children use Lego blocks guided by their imagination rather than the detailed instructions supplied in the kit. Once the functional roles of modular motifs in naturally occurring molecules have been identified, they can be added to libraries of motifs which function as Lego blocks that can be manipulated by the nanoscientist or molecular engineer. These libraries are further enriched by new motifs identified by in vitro selection methods (e.g. new aptamers, RNA-RNA interactions, ribozymes, and "communication modules").

The modular nature of RNA structure thus facilitates 3D modular design, while the sharp difference in stability between the RNA secondary and tertiary structure makes RNA fully programmable, allowing for design by reverse folding: In the 3D design phase, the molecular engineer arranges the modular motifs in 3D space so that they can mediate self-assembly in the final design. In the 2D design phase, the engineer designs the secondary structure—the pattern of double helical struts and branching motifs that connect and organize the functional motifs in the individual molecular units that will self-assemble to form the supramolecular structure. Finally, in the 1D design phase, the engineer designs the sequences to be synthesized. Each sequence is optimized to uniquely fold into its required 2D (secondary) structure (Hofacker 2003). In summary, the advantages of using RNA as a medium for nanoscience are:

1. Programmable sequence design: The free energy of formation of the secondary structure of most RNAs is an order of magnitude more favorable than that of the tertiary structure. This permits rational design at the level of sequence to achieve a desired secondary structure. Sophisticated software is available (Mfold, Sfold, etc.) to aid in designing sequences that fold uniquely into the desired structures.
2. The rapidly growing sequence and structure databases provide a growing repertoire of sequence-specific tertiary interactions and branching motifs from which to draw for tectoRNA design.
3. The relative ease of applying Darwinian in vitro selection and evolution methods makes possible the systematic discovery of new RNA-RNA interactions, RNA molecules ("aptamers") that bind a host of small molecules and new catalytic RNAs (ribozymes).
4. The modularity of 3D RNA motifs allows combinatorial joining of motifs to create new architectures, limited only by the imagination.
5. The flexibility of the RNA backbone allows for great diversity of structures and the design of intrinsically flexible molecules that exhibit adaptability upon self-assembly.

DETAILED DESCRIPTION OF THE PREFERRED EMBODIMENTS

In accordance with the foregoing summary of the invention, the following presents a detailed description of the preferred embodiments, which are considered to be the best mode thereof.

Figure 1:
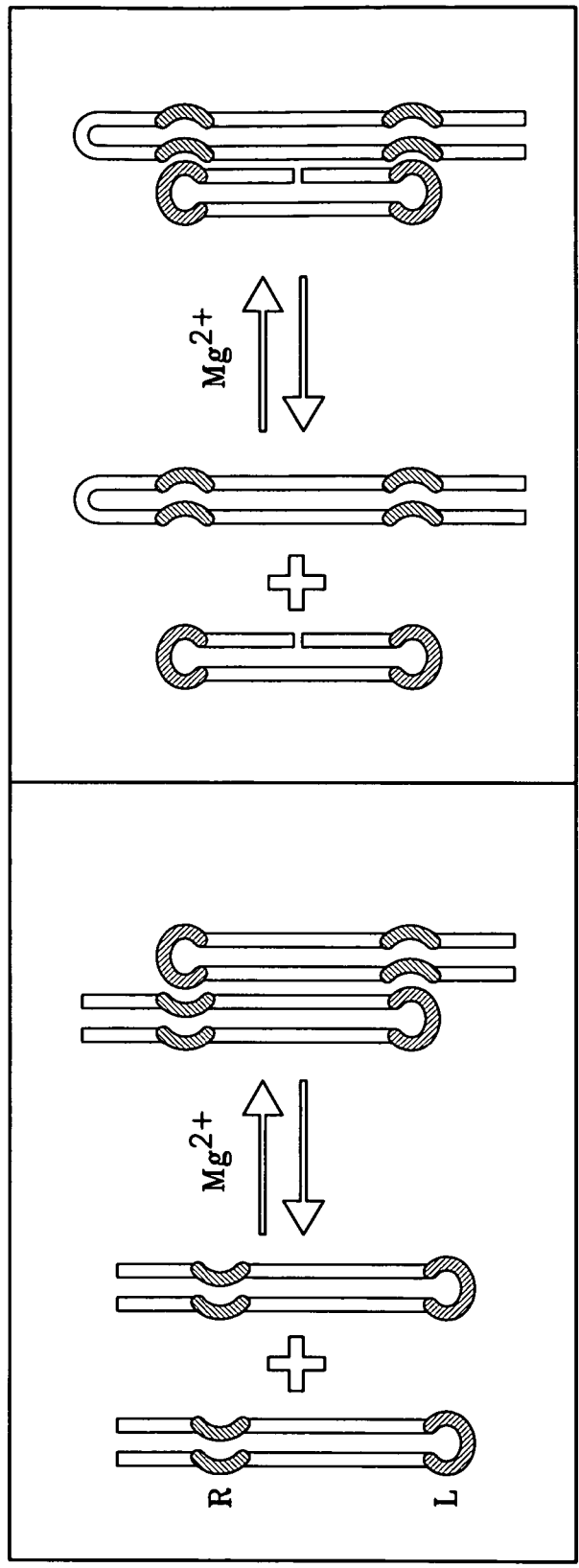
FIG. 1 shows RNA molecules designed to associate non-covalently through specific, non-covalent loop-receptor interactions, in accordance with the prior art.

Previously, principles of RNA supramolecular design ("RNA Tectonics") were used to create tectoRNA molecules that formed heterogeneous mixtures of varying length, and thus assembly was non-directional and non-conformational. Pairs of non-covalent—and thus reversible—RNA loop/receptor interactions that exploit RNA shape complementarity, base stacking interactions, and formation of non-Watson-Crick base pairs to achieve high affinity and specificity have been created (Jaeger & Leontis 2000; Jaeger et al. 2001). These interactions mediate lateral association of helical elements. RNA assembly generally requires the presence of magnesium ions or other multivalent cations (Jaeger & Leontis 2000). Using this approach, RNA molecules were originally designed such that they formed homodimers as shown in FIG. 1 (left panel). FIG. 1 shows RNA molecules designed to associate non-covalently through specific, non-covalent loop-receptor interactions, in accordance with the prior art, wherein red indicates the GAAA loop and blue the 11-nt receptor specific for GAAA (Cate et al. 1996; Cate et al. 1996). Black, vertical parallel lines indicate Watson-Crick paired anti-parallel double helices.

RNA monomers ("RNA tectons"), designed with properly spaced interacting motifs, associate with surprisingly high binding affinity ($K_d$~4 nM) in the presence of millimolar concentrations of $Mg^{2+}$. The modularity of the interaction was explored by creating the heterodimeric system shown in the right panel of FIG. 1, in which one molecule contains two loops and the other two receptors, but assembly occurs in the same way as in the homodimer system.

The dimer-forming molecules were elaborated by branching to create "divalent" RNA molecules (FIG. 2, left panel) comprising two interaction domains bridged by an anti-parallel (non-crossing) four-way junction (4WJ) module from the hairpin ribozyme (Klostermeier & Millar 2002). Each molecule can interact with two others, resulting in oligomers or equilibrium (non-covalent) polymer arrays (filaments) that assemble, as shown in FIG. 2 (middle and right panels).

Figure 2:
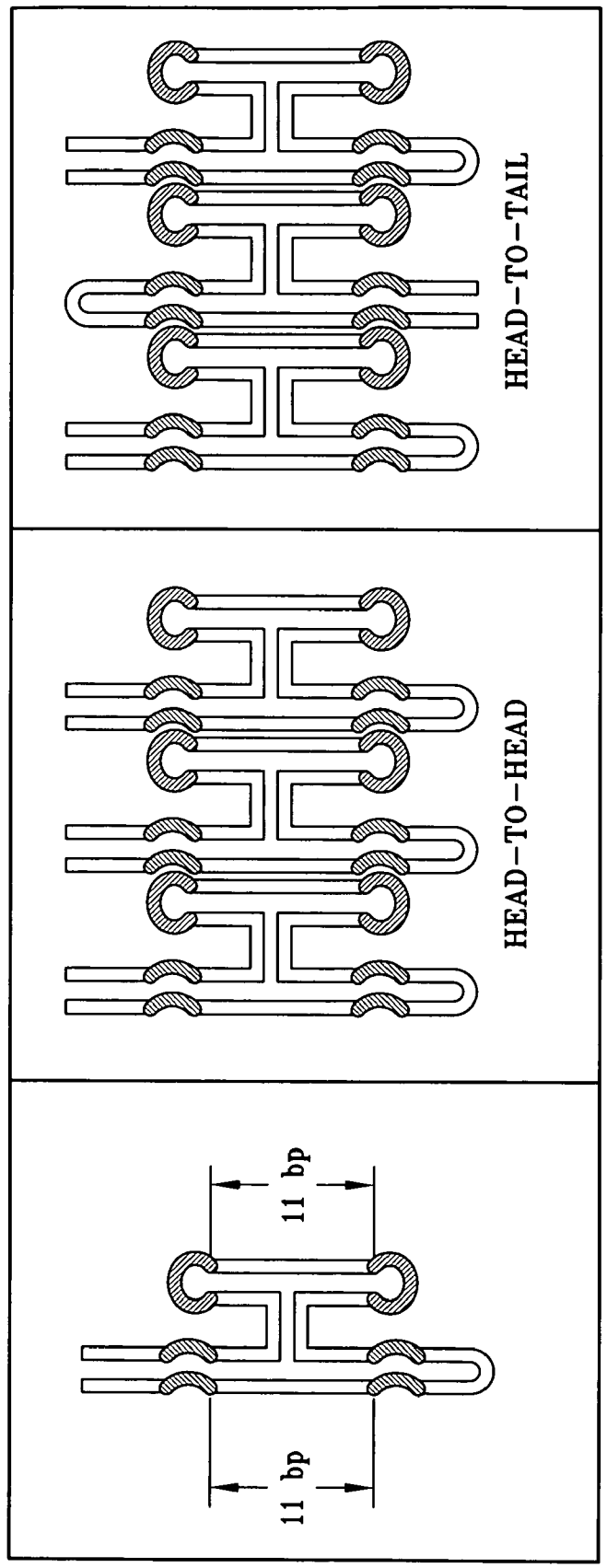
FIG. 2 shows an assembly of RNA molecules with one type of loop-receptor interaction, in accordance with the prior art.

FIG. 2 shows an assembly of RNA molecules with one type of loop-receptor interaction, in accordance with the prior art. Assembly can occur in head-to-head or head-to-tail fashion and is therefore non-directional. This structure was characterized by native polyacrylamide gel electrophoresis (PAGE) and transmission electron microscopy (TEM) in order to visualize the assembly of these first-generation tectoRNA molecules (Jaeger & Leontis 2000). However, because of two design limitations, these molecules yielded heterogeneous supramolecular assemblies: First, as only one type of loop was used in their design, these molecules assemble non-directionally in both "head-to-head" (FIG. 2, center panel) and "head-to-tail" fashion (FIG. 2, right panel). Second, because the 4WJ can isomerize, as shown in FIG. 3 (middle panel), and only a small free energy separates the two stacked 4WJ conformations, self-assembly can take place from either conformation (FIG. 3, compare right and left panels).

Figure 3:
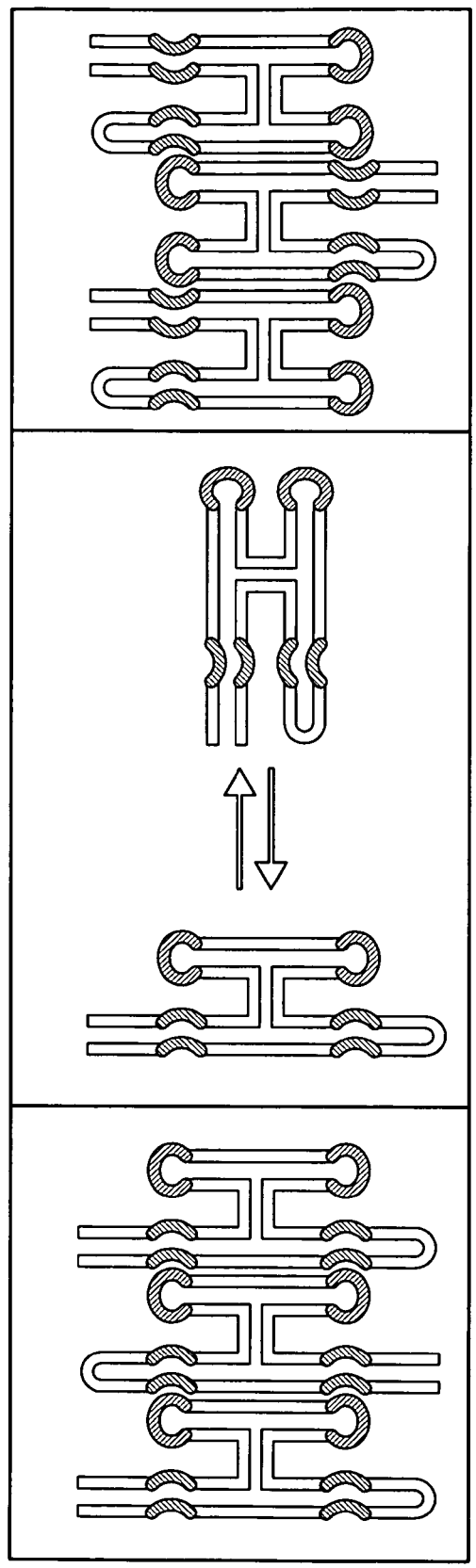
FIG. 3 shows an assembly of RNA molecules in accordance with the prior art, showing isomerization of the four-way junction resulting in alternative assembly modes.

FIG. 3 shows an assembly of RNA molecules in accordance with first-generation RNA designs, wherein isomerization of the 4WJ resulted in alternative assembly modes.

In accordance with the present invention, the first source of inhomogeneity was eliminated by designing second-generation molecules (see FIG. 4) that incorporate a second hairpin loop, GGAA (gold) and its receptor, (green). This receptor was identified by in vitro selection methods (Costa & Michel 1997).

Figure 4:
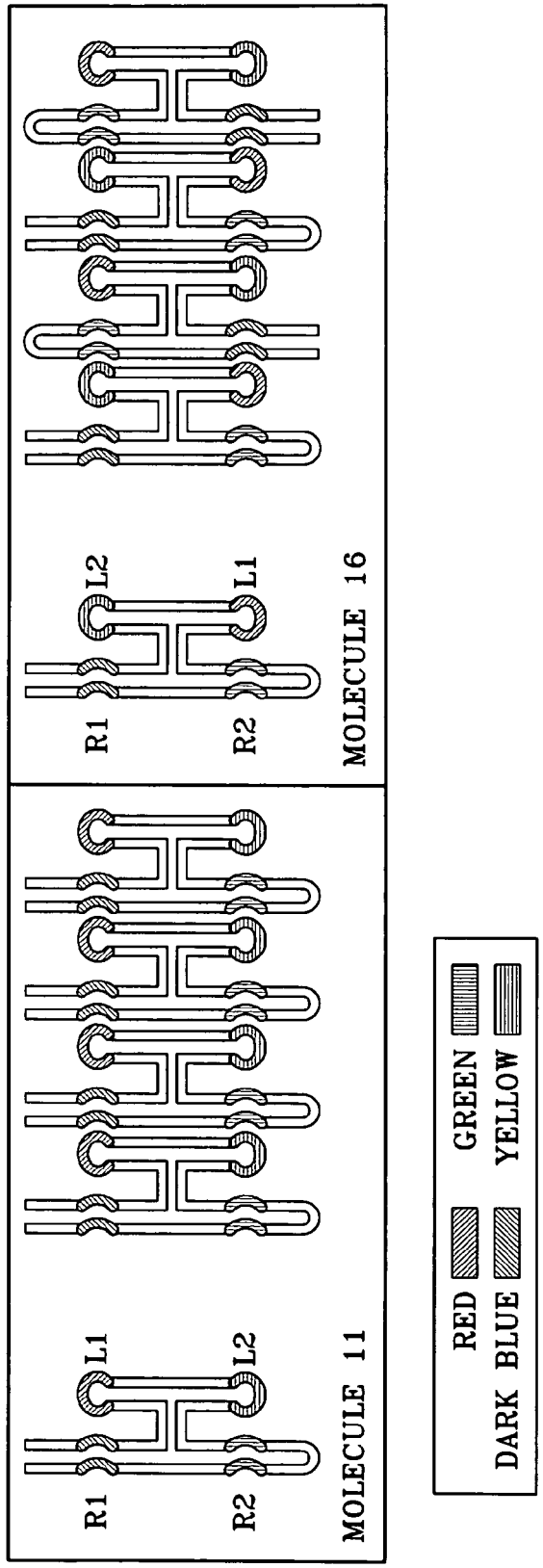
FIG. 4 shows a directional assembly of RNA molecules in accordance with one embodiment of the present invention, using two loop/receptor interaction motifs.

FIG. 4 shows a directional assembly using two loop/receptor interaction motifs. The left panel shows a head-to-head assembly while the right panel shows a head-to-tail assembly. Gold indicates GGAA loops and green indicates GGAA receptors.

In the present invention, the second source of inhomogeneity was eliminated by manipulating the positions of the interacting motifs relative to the 4WJ cross-over positions so that the motifs are properly spaced for assembly in only one 4WJ conformation (Nasalean et al. In preparation). It was found that loop-receptor motifs are optimally oriented for assembly when separated by 11 base pairs (Jaeger et al. 2001). Thus, the molecule shown in FIG. 5 (center panel) assembles preferentially from the 4WJ conformation shown in the left panel, in which the interacting motifs are separated by 11 base pairs.

Figure 5:
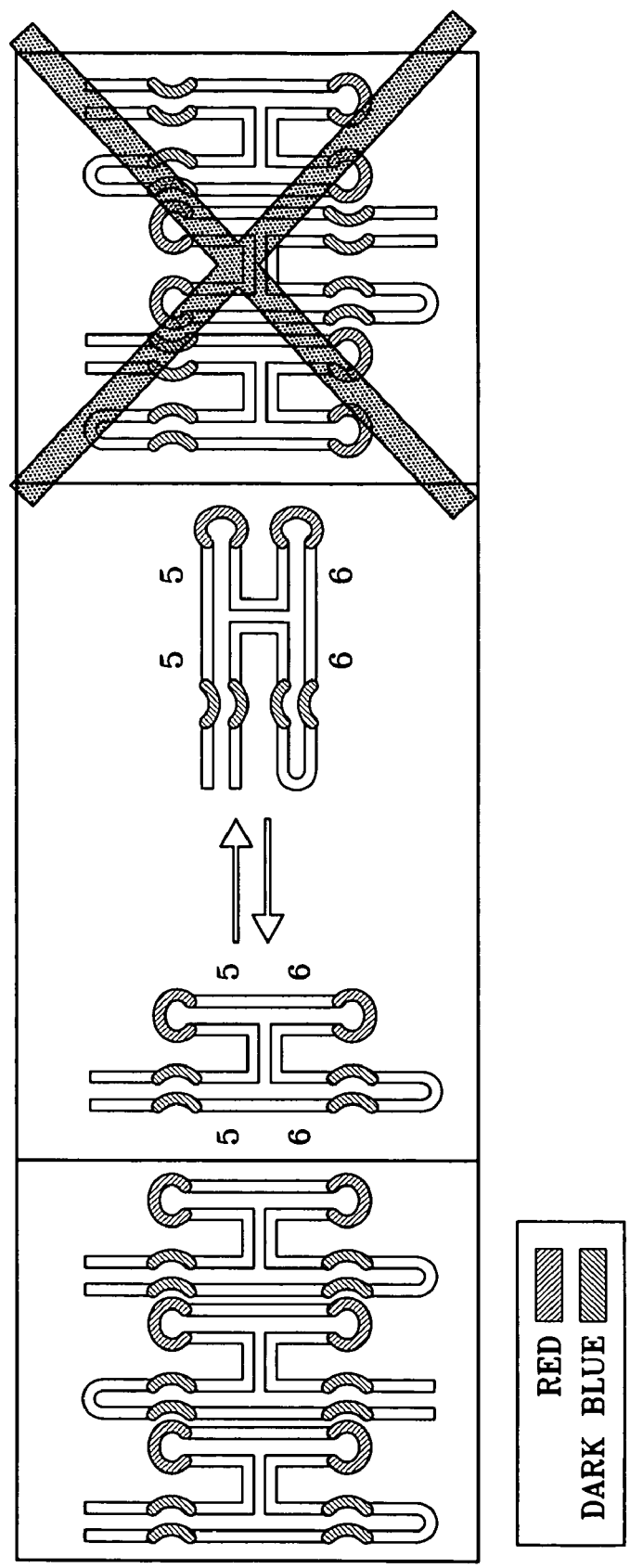
FIG. 5 shows a RNA molecule designed to assemble preferentially by loop-receptor interactions from one of the four-way junction conformations, in accordance with one embodiment of the present invention.

FIG. 5 shows an RNA molecule designed to assemble preferentially by loop-receptor interactions from one of the 4WJ conformations (center panel). In the conformation on the left, the interacting motifs in each helical stacking domain are separated by 5+6=11 nucleotides, and are thus ideally positioned for association (left panel). In the alternate 4WJ conformation, two motifs are separated by 10 and two by 12 nucleotides, disfavoring assembly from this conformation (right panel).

Figure 6:
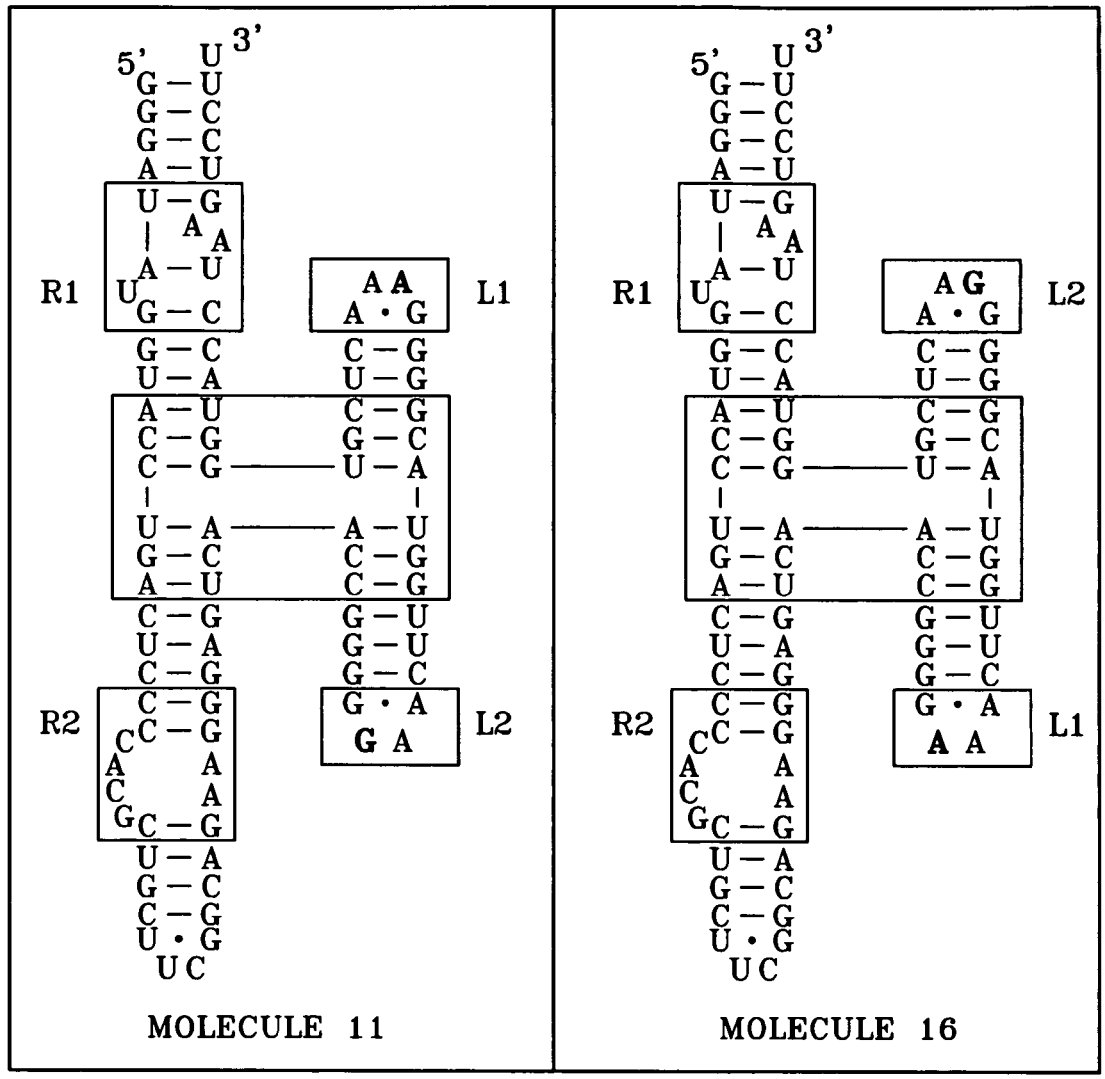
FIG. 6 shows RNA molecules designed for directional binding from only one four-way junction conformation, in accordance with one embodiment of the present invention.

In applying the new RNA design principles of the present invention, directional assembly and control of the junction conformation, two nearly identical molecules (Molecules 11 and 16) were designed that differ structurally only in the positions of the loops (FIG. 4 and FIG. 6). A small difference in sequence between the two molecules—just two nucleotides (i.e., GAAA vs. GGAA)—produces radically different assembly properties. Molecule 16 produces very long linear arrays, while 11 assembles cooperatively to form compact oligomers of definite stoichiometry. These complexes are trimeric as described herein. (At high concentrations, 11 also forms a higher MW species.) The cooperative oligomerization of 11 was inferred from the failure to observe dimeric species, even at sub-nanomolar concentrations and from competition experiments showing that high concentrations of 16 are required to disrupt 11 complexes (Hassan et al. M. S. Thesis, Bowling Green State University). Moreover, complexes of 11 are quite stable and exchange slowly with added radioactively labeled 11. The results obtained with Molecules 11 and 16 demonstrate that one can exercise remarkable control over the self-assembly process by carefully positioning interacting motifs and applying the new design principles. More than 30 molecules have been studied based on the 4WJ core motif, varying the arrangements of the loop and receptor motifs and their distances from the junction crossover point. The key concept that emerges from these studies is the role played by orientational compensation in determining the nature of the supra-molecular assemblies resulting from each molecular design. Application of this concept allows fundamental control over the supra-molecular assembly process.

FIG. 6 shows a comparison between two different RNA molecules (referred to as Molecule 11 and Molecule 16) designed for directional binding from only one 4WJ conformation. Molecule 11 assembles without orientational compensation and forms closed complexes. In contrast, Molecule 16 assembles with head-to-tail compensation to form long fibers. The sequences of these molecules differ at only two nucleotides (shown in red), demonstrating the remarkable control of self-assembly of RNA that is possible with the present invention.

Orientational Compensation

As tecto RNA molecules are asymmetric, chiral objects, when two molecules such as Molecule 11 assemble head-to-head and right-to-left, the translation of the second molecule is accompanied by rotations that are not compensated when successive units are added and a curvature is produced in the assembly. In the general case, the curvature is not confined to a single plane and helical arrays result, but when assembly is confined to a single plane, closed complexes result. It has been found that orientationally uncompensated molecules like Molecule 11 generally exhibit sharp, discrete bands on native gels, and appear as globular clusters or "rosettes" by TEM, indicating that such molecules form closed complexes.

On the other hand, for head-to-tail assembly, orientational compensation occurs. Molecules that assemble in this manner (such as Molecule 16) produce diffuse, concentration-dependent bands on native gels. At nanomolar RNA concentrations, these molecules migrate on native gels with high mobility; at micro molar concentrations, however, they exhibit very low mobilities, remaining in or near the loading wells of native 7% polyacrylamide electrophoresis gels. Under TEM one observes long, relatively straight filaments for these molecules.

In a head-to-tail assembly, each monomer added to the assembly is rotated 180° about an axis parallel to the direction of polymerization. In left-to-left/right-to-right assembly, each monomer is rotated 180° about an axis perpendicular to the direction of polymerization. For a doubly compensated molecule, the two successive rotations about orthogonal axes lying in the same plane are equivalent to a 180° rotation about an axis perpendicular to the plane of the monomer unit.

Figure 7:
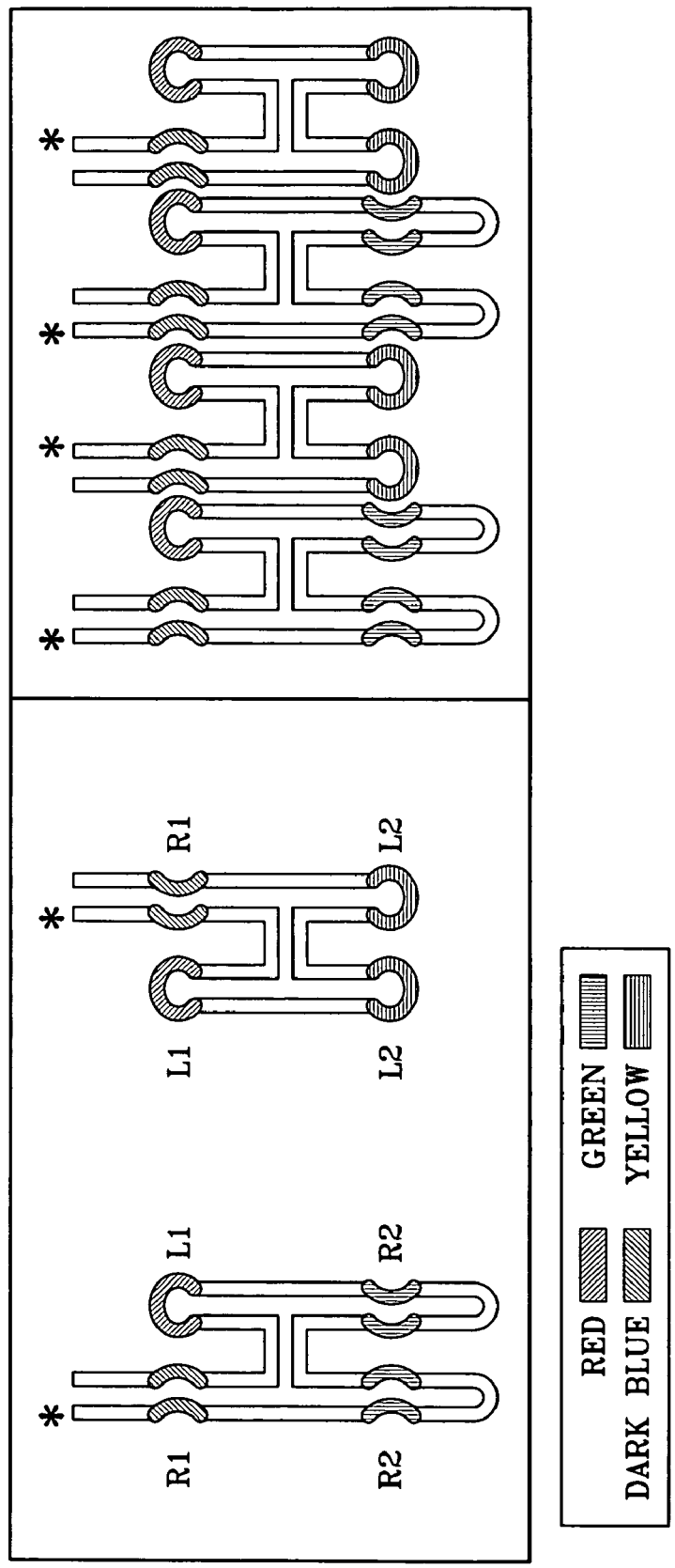
FIG. 7 shows RNA molecules of a design that assemble with left/right orientational compensation, in accordance with one embodiment of the present invention.

FIG. 7 shows RNA molecules of a design that assemble with left/right orientational compensation. The asterisk (*) indicates the 5'-end of each molecule. The second molecule must rotate 180° about an axis in the plane of the molecule and perpendicular to the axis of propagation. This design showed that equilibrium polymers are also obtained by left/right compensation.

Left/Right Compensation

One set of molecules prepared in accordance with the present invention assemble with left/right compensation (see FIG. 7). Neither molecule self-associates, but equimolar mixtures produce smeary, concentration-dependent bands on native gels, as expected for fiber-forming molecules.

Double Compensation

Figure 8:
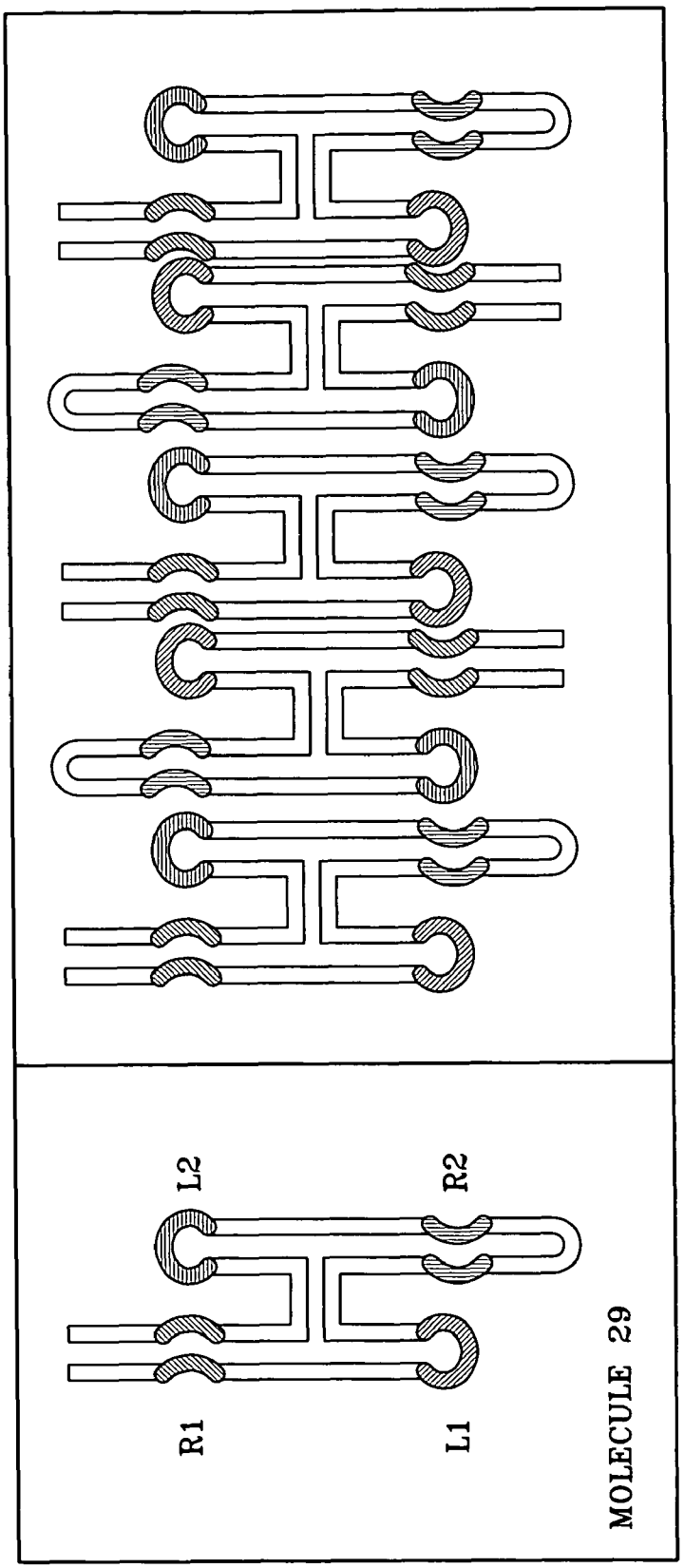
FIG. 8 shows RNA molecule assembles with both head/tail and left/right compensation, in accordance with one embodiment of the present invention.
Figure 9:
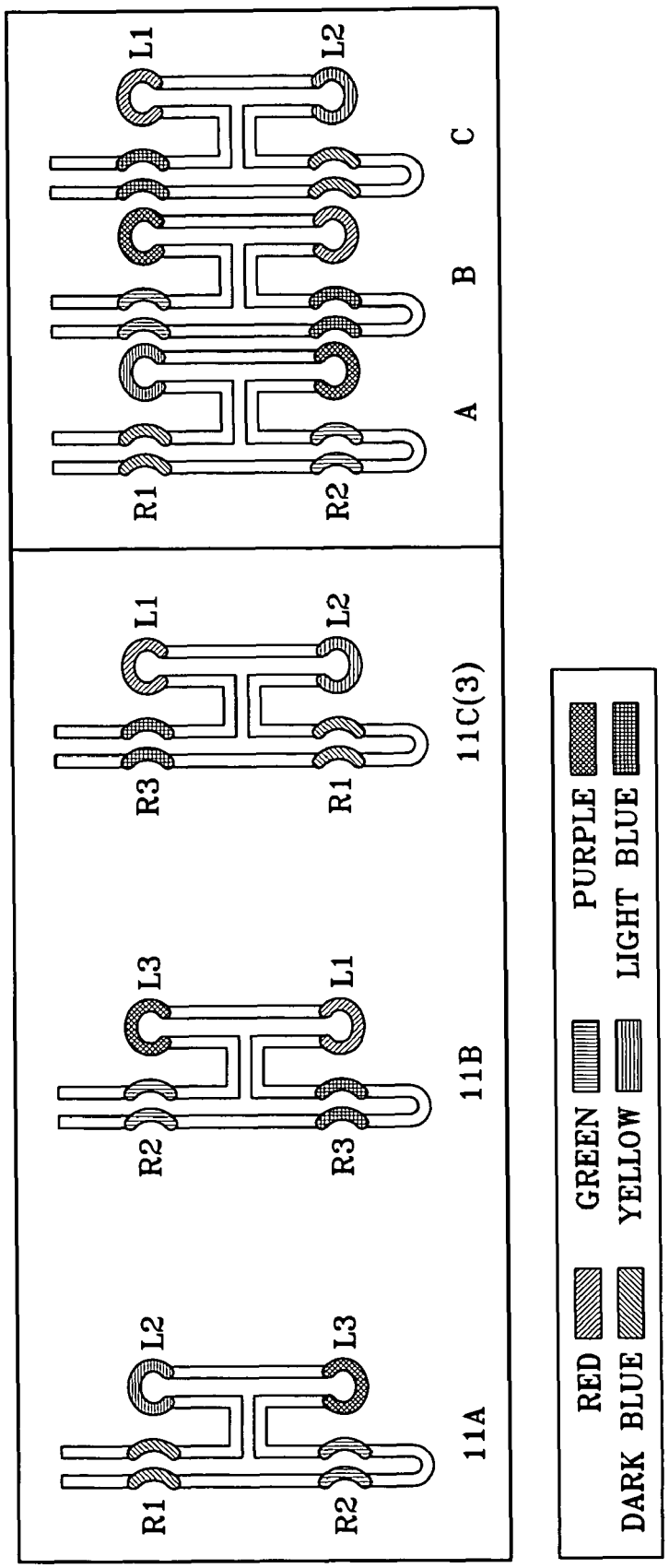
FIG. 9 shows molecules designed by using three specific loop-receptor motifs to determine the stoichiometry of complexes in accordance with one embodiment of the present invention.

FIG. 8 shows Molecule 29 assembles with both head/tail and left/right compensation. It forms closed complexes like uncompensated molecules (e.g. molecule 11). Molecule 29 is an example of one designed in accordance with the present invention which assembles with both head/tail and right/left double orientational compensation, as shown in FIG. 9. It produces a discrete band on native gels with mobility substantially slower than that of 11. Thus, it appears to form closed complexes like an uncompensated molecule, but with greater stoichiometry.

Characterization of Molecule 11

Even though x-ray structures exist for each modular component that was used to construct molecule 11, its ability to form closed complexes was not anticipated from 3D modeling, because the conformation of its 4WJ in the crystal structure of the hairpin ribozyme precludes the formation of a closed complex. Thus, the 4WJ probably undergoes substantial conformational adjustment when molecule 11 assembles to form closed complexes. The angle between the two helical stacking domains joined by the junction most likely decreases to allow the interacting motifs to form closed complexes. The ability of tectons like molecule 11 to adapt conformationally upon assembly is consistent with the known flexibility of DNA and RNA 4WJ from studies of solution dynamics (Hohng et al. 2004). FRET experiments may be used to detect conformational changes that occur in molecule 11 during self-assembly using the trimer system described below.

The observation of closed complexes for molecule 11 by TEM suggests that each molecule in the complex interacts with two others. This can account for the observed cooperativity of assembly and the increased stability of the complex (Goodsell & Olson 2000). Open complexes of n subunits (n-complexes) have n–1 intersubunit interactions, while closed n-complexes result from n interactions. The overwhelming majority of biological proteins exist as oligomers and many form cooperatively bound closed complexes. This endows these proteins with many advantageous properties: speed and accuracy of synthesis, efficient binding of ligands and substrates, improved allosteric regulation, reduced surface area, and increased stability (Goodsell & Olson 2000). Our discovery of tectoRNA that form cooperative complexes thus creates the possibility of designing RNA molecules that share these properties. The present proposal focuses on characterizing cooperatively assembling RNA systems and exploring the usefulness of their properties.

Experiments were carried out to measure the kinetics of exchange of free and complexed subunits (Hassan & Nasalean, unpublished). Small amounts of radioactively labeled 11 were added to preformed complexes of unlabeled Molecule 11 in magnesium-containing buffer. Even at 30° C., exchange takes many hours to complete, evidence of the stability of cooperative RNA complexes. These experiments may be repeated with the new trimer system for Molecule 11, described below, which were used to determine the stoichiometry of the oligomeric complexes, and which is necessary to carry out detailed thermodynamic and kinetic experiments.

Stoichiometry of Cooperative Complexes of Molecule 11

To determine the stoichiometry of complexes of Molecule 11, crucial data for further progress, sets of molecules were designed with complementary interaction interfaces, using three pairs of specific loop-receptor motifs. The first set of molecules (11A, 11B, and 11C-trimer) is shown in FIG. 9. These molecules were designed so that each is incapable of interacting with itself, but binds to each of the other two molecules in a directional manner to potentially form a closed complex of three, or possibly six, monomer units.

FIG. 9 shows molecules designed by using three specific loop-receptor motifs to determine the stoichiometry of Molecule 10 complexes.

Figure 11:
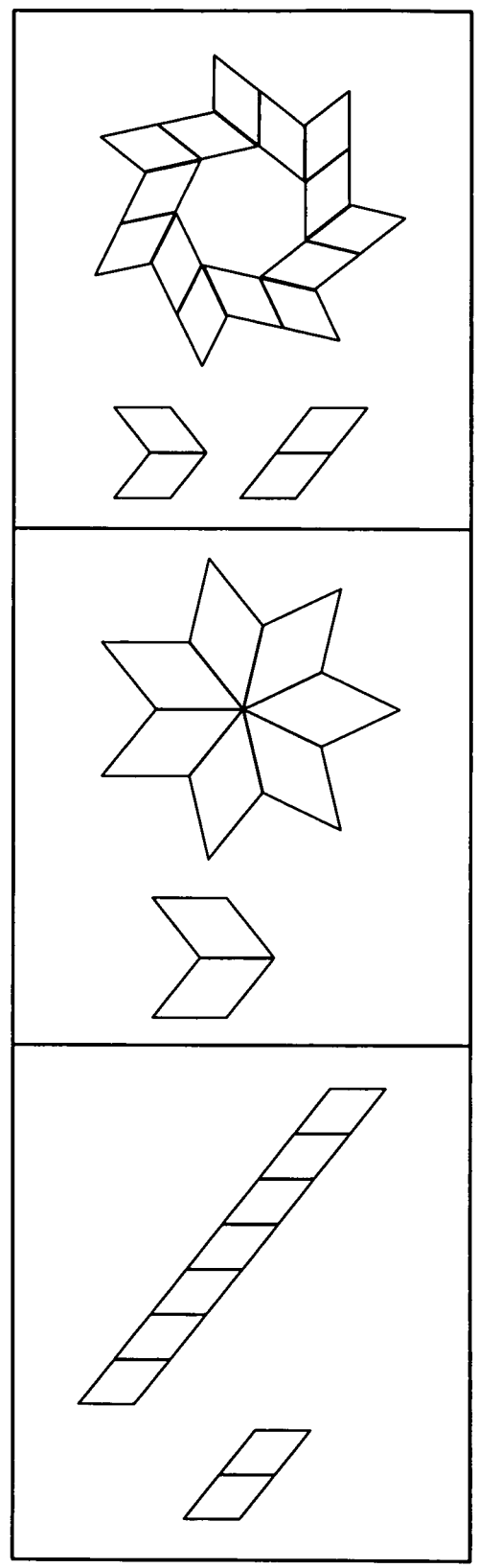
FIG. 11 shows the formation of closed complexes by mixing monomer units that assemble head-to-head with monomer units, in accordance with another embodiment of the present invention.

Other molecules were designed, as shown in FIG. 11, to form stoichiometries up to six. Thus, molecules 11A, 11B, 11C, and 11D(4) have the appropriate interfaces to combine to form tetramers, 11B(5), 11C, 11D, and 11E, and 11F can combine to form pentamers, while 11A, 11B, 11C, 11D, 11E, and 11F can form hexamers.

All combinations were examined by native gel electrophoresis, but only 11A, 11B, and 11C(3) combined in a cooperative fashion to form stable complexes with the same electrophoretic mobility as complexes of 11. Native PAGE experiment shows cooperative assembly of 11A, 11B, and 11C(3) (lanes 18 and 19) to form a trimer complex with the same electrophoretic mobility as the Molecule 11 complex (lanes 3-5). Individual molecules 11A, 11B, and 11C(3) have little tendency to self associate.

Expandable Closed Complexes

To move beyond trimer complexes, the present invention also includes a method for developing the constructs illustrated schematically in the first two panels of FIG. 11 using 2D tiles that assemble either head-to-tail (compensated) to form linear arrays or head-to-head (uncompensated) to form closed complexes. For example, should one may alternate monomer units that assemble head-to-head with units that assemble head-to-tail as illustrated in the right panel of FIG. 11. This method accordingly provides for the expansion of the present invention to produce larger complexes consisting of more subunits. FIG. 11 shows the expansion of closed complexes (middle) by mixing with monomers that assemble Head-to-Tail (left) to produce expanded complexes (right).

Experiments indicate that something like this occurs with certain tectoRNAs. Native gel electrophoresis of 11 mixed with 16 shows that slower-moving complexes replace the trimer complexes formed by 11 and the long fibers formed by 16. Both molecules are present in these complexes. No protein is known to be able to change the size of its complexes in this way.

The positions of R1 and R2 and of L1 and L2 are switched in Molecule 16 to design Molecule 40, which also assembles by Head-to-Tail compensation, and, as expected, also forms filaments. Interestingly, mixing 16 and 40 gave discrete bands of identical mobility as those produced by 16+11 with estimated stoichiometries of six to eight monomer units. Native gel shows that mixtures of 11/16 and 16/40 form discrete complexes larger than the closed trimer complexes of 11 and that contain both 16 and 11 or 16 and 40, respectively, as indicated by radiolabeling. Concentrations are in micromolar for added unlabelled RNA.

Figure 12:
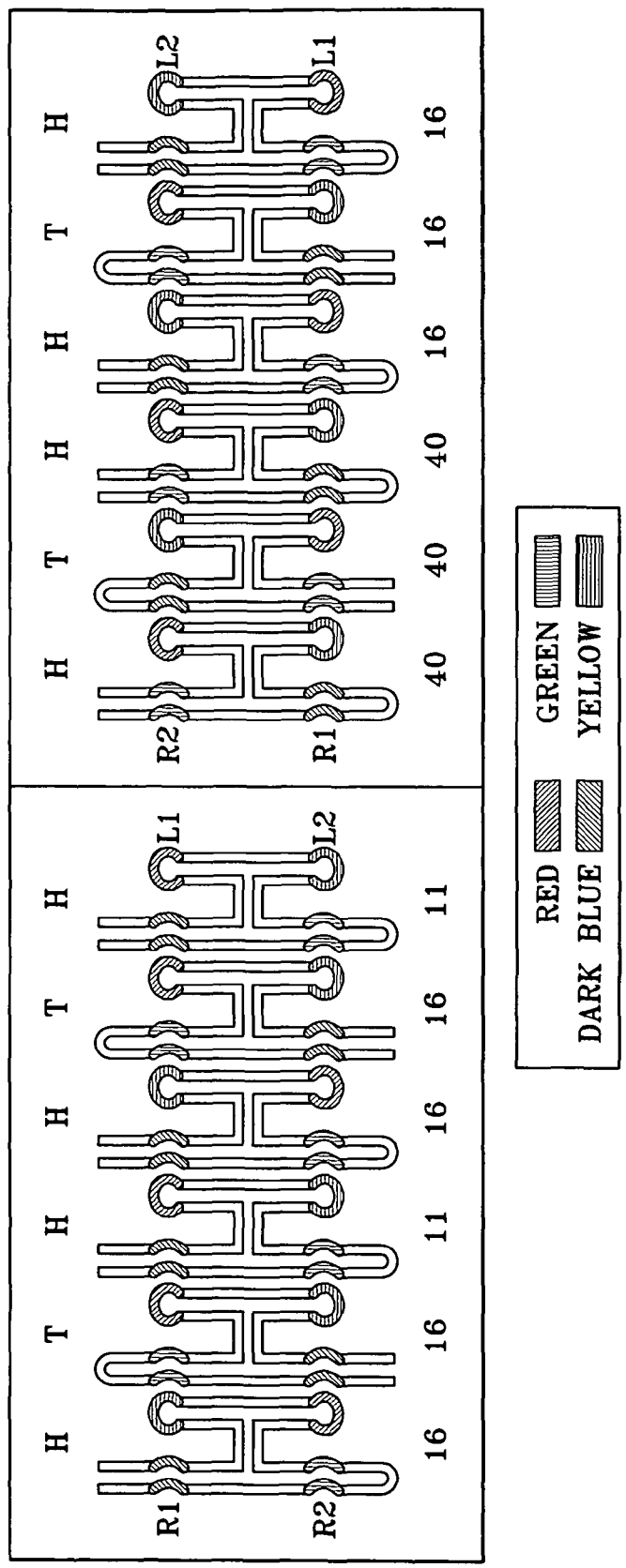
FIG. 12 shows that identical hexameric complexes can be formed by three different RNA monomers, in accordance with yet another embodiment of the present invention.

Further inspection indicates that neither mixture can give closed trimer complexes because of the topology of the loops and receptors, regardless of the way the monomers are combined. For 16/40/16, for example, the loops and receptors are not properly oriented to close the complex, while for 16/11/16, two of the interactions compensate, also making it impossible to close the complex. Extending this analysis further shows that no odd-number closed complex can be formed by 16+40, in any combination. However, analysis also indicates that both mixtures may produce closed hexameric complexes in one of several ways. Likely sequences of six monomers that are exactly equivalent are shown in FIG. 12. It is expected that each will form closed complexes because the loops and receptors of the first and last monomer align properly and a majority of monomers are oriented in the same direction (four head and two tail). There are other possible sequences of monomers that may give closed complexes.

FIG. 12 demonstrates that identical hexameric complexes (possibly closed) can be formed by RNA molecules 16+11 and by 16+40.

Structures in accordance with the present invention may be studied to test different sequences of compensated and uncompensated interactions to determine which ones form closed complexes, and to determine the stoichiometries of the complexes. If desired, new closed complexes in accordance with the present invention may be identified by native gel electrophoresis and characterized by TEM studies to determine their dimensions and shapes. The relative positions of interacting motifs relative to the 4WJ may be varied to affect stoichiometry, cooperativity and stability of closed complexes.

Figure 10:
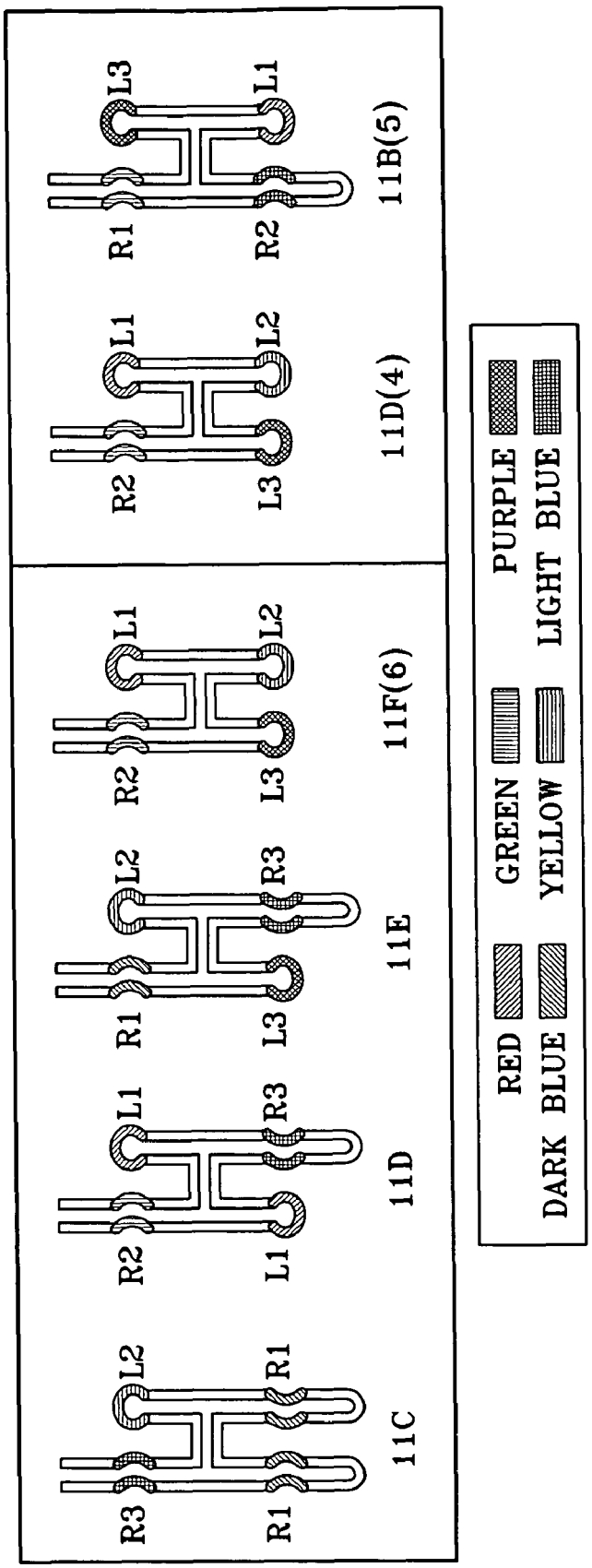
FIG. 10 shows other molecules designed in accordance with other embodiments of the present invention, to demonstrate stoichiometries up to six, including tetramers, pentamers and hexamers.

By combining three loop/receptor motifs, one may generate six different directional interaction interfaces and use these to create molecules that associate unambiguously in sequential order, as was done to determine the stoichiometry of molecule 11 trimers, and as may be done to molecule 29. To determine the nature of the expandable complexes formed by 11+16 and 16+40, one may also prepare two new sets of six molecules, 16A to 16F and 40A to 40F by modifying the 11A to 11F series of molecules (FIGS. 9 & 10) as shown for 11A in FIG. 13. Switching the positions of the motifs on the helical stacking domain on the right side of molecule 11A produces 16A, while switching the motifs on the left side produces molecule 40A. In this way, sets of molecules may be generated that can be "mixed and matched" in many ways to determine which combinations give discrete complexes of different sizes. The native gel electrophoresis experiments may then be followed by transmission electron microscopy studies of those complexes that produce discrete complexes on gels, so as to elucidate rules of assembly involving combinations of compensated and uncompensated interactions.

Figure 13:
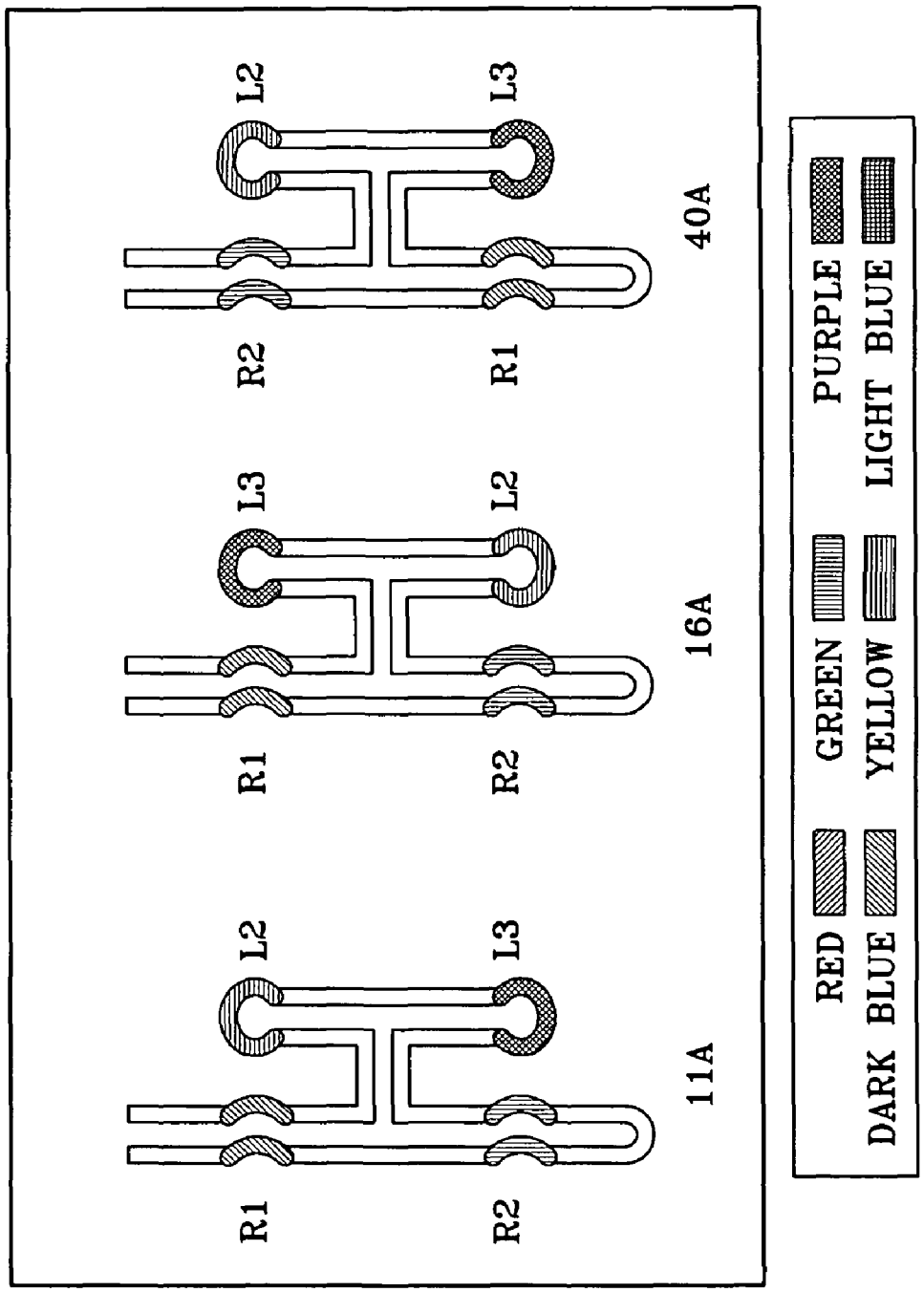
FIG. 13 shows an example of the relationship between molecules in the three different series of RNA monomers, in accordance with still another embodiment of the present invention.

FIG. 13 shows an example of relationship between molecules in the 16A-16F and 40A-40F series to molecules in the 11A-11F series. Shown are 11A (see also FIG. 10), 16A, and 40A.

The 11/16/40 series of molecules share the same positioning of the motifs relative to the 4WJ (FIG. 6). The junction is 5 bp from the motifs in the upper half of each molecule and 6 bp from those in the lower half. These distances are crucial for determining the angles at which monomers associate and thus whether closed complexes form and how large they are. These distances may be systematically varied to determine which combinations give closed complexes and to determine the effects of these changes on the stoichiometries of complexes. This may be done by modifying the 11A-F, 16A-F and 40A-F series of molecules.

Isothermal Titration Calorimetry (ITC) and Differential Scanning Calorimetry (DSC) studies of selected cooperative complexes, such as 11A/11B/11C(3) may be carried out on all pairs and triples (all orders of addition) to determine the cooperativity of the complex. For example, 11C(3) may be added to the complex of 11A+11B and the energy parameters obtained will be compared to the pairwise combinations of 11A+11B, 11A+11C(3). For instance, in those assemblies involving double compensation, the cooperativity of the assembly may be measured by ITC.

Other thermodynamic and biophysical measurements may be carried out to elucidate the behavior of these systems (e.g. DSC, CD, etc.) as desired.

The kinetics of monomer exchange for 11A/11B/11C and other cooperative complexes may be measured by studying the exchange of added radioactively labeled monomers to preformed unlabeled complexes, and monitoring by gel electrophoresis. The development of the cooperative trimer system is key to the success of these experiments.

FRET experiments may be used to measure conformation changes induced by assembly into closed complexes. For instance molecule 11A with fluorescein (F) and 11C(3) with TAMRA (T) (FIG. 14) and observe FRET from F to T when the molecules are bound to form dimers. Further, molecule 11B may be added to see whether increases in FRET efficiency occur, as expected when the cooperative complex forms.

Figure 14:
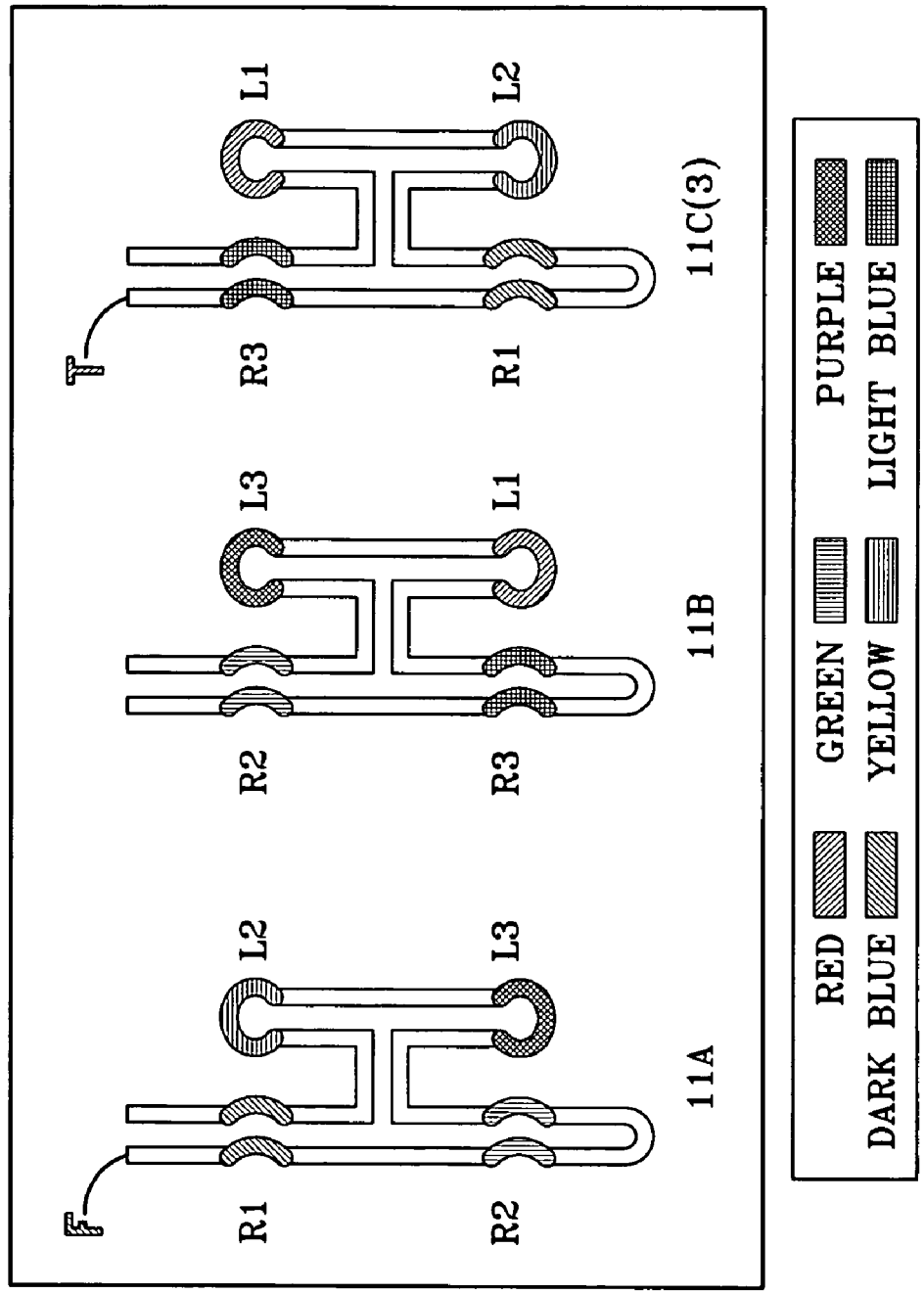
FIG. 14 shows an example of an RNA hexameric complex in accordance with still another embodiment of the present invention.

FIG. 14 shows the 11A/11B/11C(3) system that permits the study of conformational changes upon closed complex formation using FRET by individually labeling molecules with a donor (F) or acceptor (T) fluorescent molecule.

The present invention also permits that design and assembly of molecules with rigid junctions and explore the effects of junction rigidity on stoichiometry, cooperativity and stability of closed complexes.

For instance, 3D modeling indicates that formation of cooperative complexes by 11 requires a conformational change at the 4WJ to bring the two helical domains close to parallel. Thus, reducing the conformational entropy of the 4WJ by making it more rigid may increase the stability of the closed complex and improve tectoRNA derived from 11 as platforms for nanotechnology applications. For DNA, 4WJ rigidification has been achieved using double cross-over motifs, making possible creation of rigid tiles for 2D tiling and algorithmic computation. Strategies for rigidifying or locking the conformations of RNA 4WJs that may be pursued include: a) Use of Double Junctions as in DNA; b) Use of Loop E/receptor minor-groove motifs (as found in ribosome); c) Use of pseudo-knot interactions.

Figure 15:
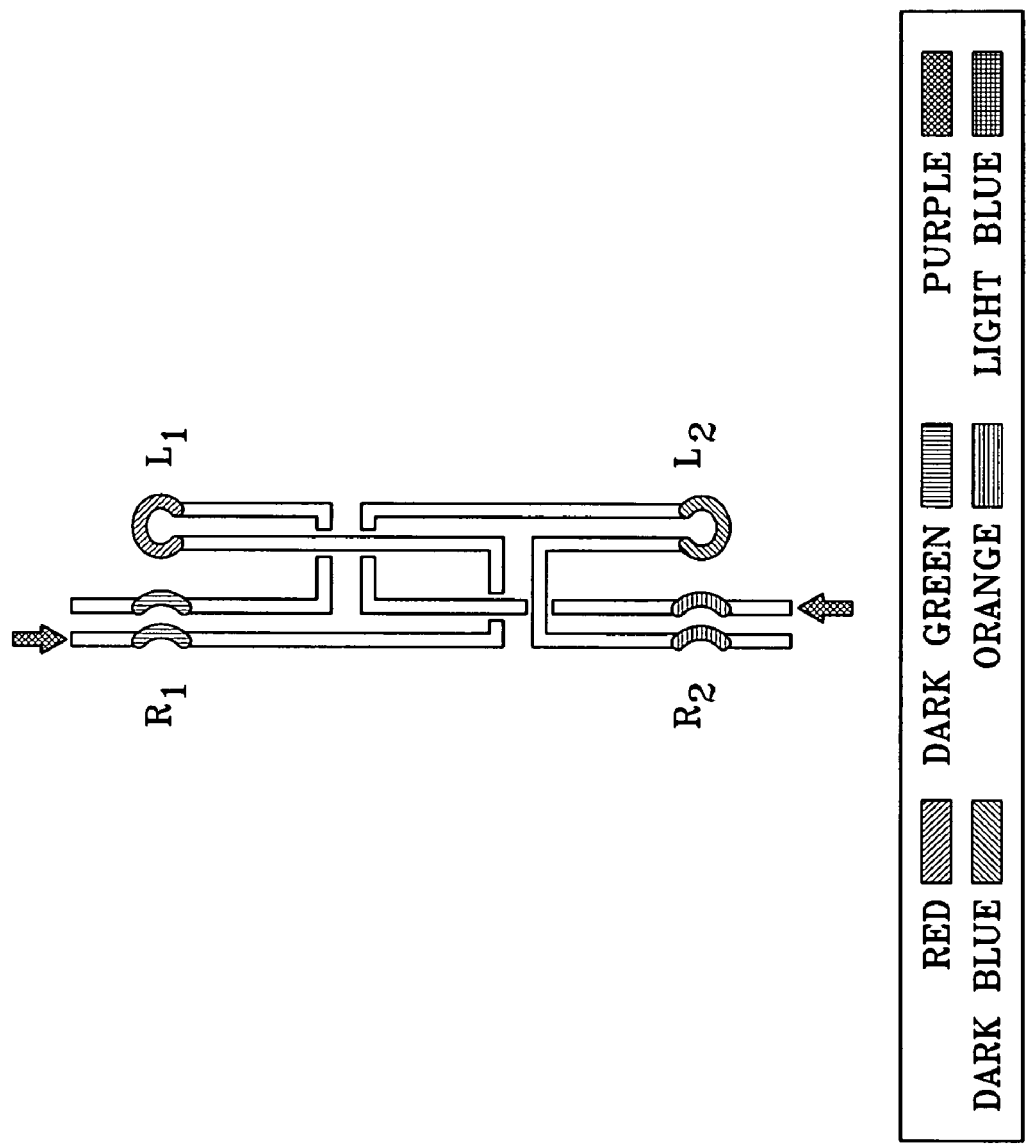
FIG. 15 shows the design for two-stranded tectoRNA module with a DAO type double junction, in accordance with still another embodiment of the present invention.

FIG. 15 shows the design for two-stranded tectoRNA module with DAO type double junction. Arrows indicate 5'-ends of strands.

Molecular modeling studies have been carried out to determine the best way to design molecules using this approach. Because RNA forms A-type helices, sequence and structure designs developed for B-type DNA must be modified for RNA, guided by 3D modeling. These modeling studies using the flexible 4WJ from the hairpin ribozyme, indicate that a DAO type double junction should be feasible with RNA, although the optimal design may not be symmetric with regard to the lengths of the helical elements separating the junction motifs (FIG. 15). While this approach requires synthesizing and assembling two RNA strands to create a single monomer unit, it has the advantage of allowing one to create rigid modular units which like their DNA counterparts are suitable for 2D or even 3D tiling of space. Alternative approaches may also be realized with a single strand.

Another aspect of the present invention is to use "kissing" hairpins to create the second bridging helix of the double junction. Crystal structures exist for these motifs, including that of the dimerization initiation site (DIS) of HIV (Ennifar et al. 2001). Alternatively sequences of hairpin-hairpin pseudoknots from the ribosome such as the pseudoknot formed by the hairpin loops located at 418-423 and 2444-2449 in the H.m. 50S ribosome can be used.

Finally, one may also use a 4WJ, such as the one formed by helices 56-59 in 23S rRNA that incorporate loop E motifs to mediate minor groove interactions between neighboring helices. Such 4WJ have nearly parallel helical stacking domains, as may be desired.

Accordingly, one may harness the cooperative self-assembly of tectoRNA complexes such as 11A/11B/11C to create platforms for building nanoscale devices such as biosensors.

In addition, tectoRNA complexes such as 11A/11B/11C may be developed as general platforms for selecting: (1) new specific loop-receptor interactions (2) more general RNA-RNA interactions, such as internal loop-internal loop; (3) improved aptamers that bind with higher affinity and cooperativity.

Cooperatively assembling tectoRNA molecules may in turn be used as scaffoldings to measure weak tertiary interactions in RNA. This may be applied to quantify weak interactions—for example the cooperative system 11 will be used to measure weak binding of GNRA loops to minor grooves—to quantify the specificity of binding GYGA vs. GYAA to minor grooves of different helices. Accurate knowledge of thermodynamic parameters for RNA tertiary interactions is crucial for advancing tectoRNA science.

Figure 16:
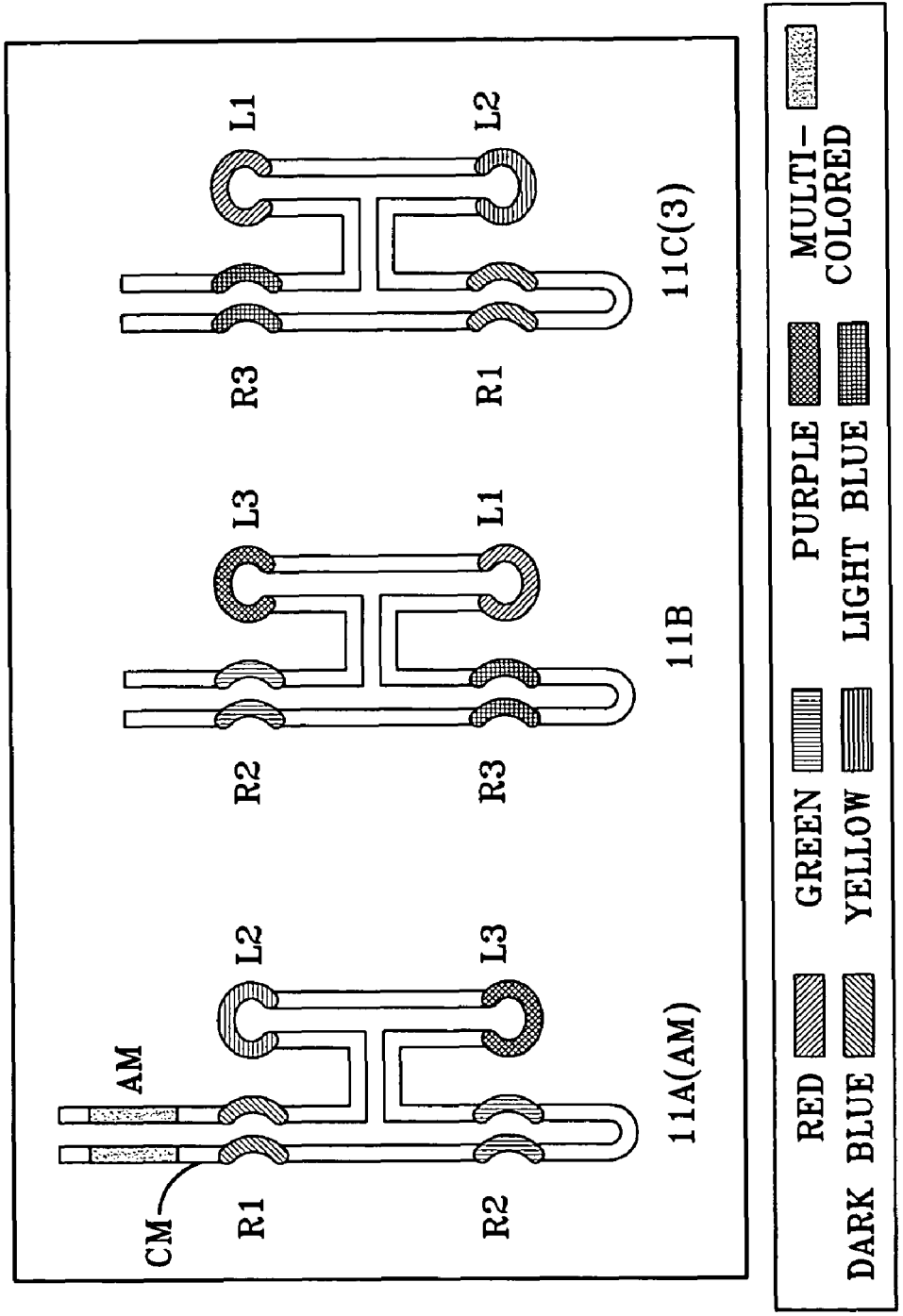
FIG. 16 shows the coupling of an aptamer module to loop-receptor structure via a short communication module to couple analyte binding to a cooperative tectoRNA self-assembly, in accordance with still another embodiment of the present invention.

The cooperative tectoRNA complex 11A/11B/11C(3) provides a novel molecular platform adaptable to a wide range of applications. One of the principal features of the present invention is based upon the harnessing of the cooperative self-assembly of these RNA complexes to drive desired molecular recognition events. For example, RNA aptamers generally bind their targets with considerably lower affinity than do antibodies, their protein cousins. Thus, it is highly desirable to find general ways applicable to many different aptamers to increase the affinity of aptamers for their targets. Titration experiments have shown that the trimer formed cooperatively by 11A, 11B, and 11C(3) is more stable than any of the dimers, 11A/11B, 11A/11C(3), or 11B/11C(3). An aptamer module (AM) that recognizes a target of interest can be incorporated into a tectoRNA such as 11A as shown in FIG. 16, positioned close to one of the loop-receptor modules, and coupled by a communication module (CM) (Stojanovic & Kolpashchikov 2004). Computer modeling and empirical experimentation will determine the best locations for AM and CM—for example flanking a loop receptor as shown or located between a loop receptor and the 4WJ motif.

FIG. 16 shows the coupling of Aptamer Module (AM) to loop-receptor R1 via a short Communication Module (CM) in 11A(AM) to couple analyte binding by AM to cooperative tectoRNA self-assembly. The communication module is intended to couple RNA assembly to analyte binding. The analyte binds to and stabilizes the aptamer module by induced fit (Hermann 2000), which in turn stabilizes the loop-receptor module via the communication module (CM), facilitating trimer assembly. Precedent for the proposed approach of FIG. 16 is provided by the recent demonstration that the aptamer for Malachite Green (MG) can be coupled to aptamer modules for non-fluorescent molecules of biological interest such as ATP using a short, unstable helix as communication module (Stojanovic & Kolpashchikov 2004). Versatile communication modules, such as those recently obtained by in vitro selection and shown to couple aptamer binding and enzymatic activity for several different ribozymes (Kertsburg & Soukup 2002), may also be used. The resulting constructs may be studied to determine (1) how RNA self-assembly is modulated by aptamer binding its target; (2) the magnitude of changes in aptamer binding affinities; (3) changes in the range of analyte concentration at which the aptamer responds—i.e. its sensitivity to tuning by RNA self-assembly; and (4) cooperativity of analyte binding, especially when aptamer binding sites are also incorporated in 11B and 11C(3). To obtain proof of principle, one may use well-characterized aptamers such as the malachite green aptamer, which binds and enhances the fluorescence of MG and several of its fluorescent analogues and thus provides for easily detected fluorescent reporting of target binding.

Aptamer-target interactions can be transduced into electrochemical, mechanical, piezoelectric or fluorescent signals. Fluorescence signaling is perhaps most desirable because of the convenience of detection, diverse measurement methods, and availability of a large selection of fluorophores and quenchers for nucleic acid modification. General methods for transducing aptamer-target interactions into fluorescent signals based on structure-switching were recently described and are applicable within the tectoRNA format (Nutiu & Li 2004).

Figure 17:
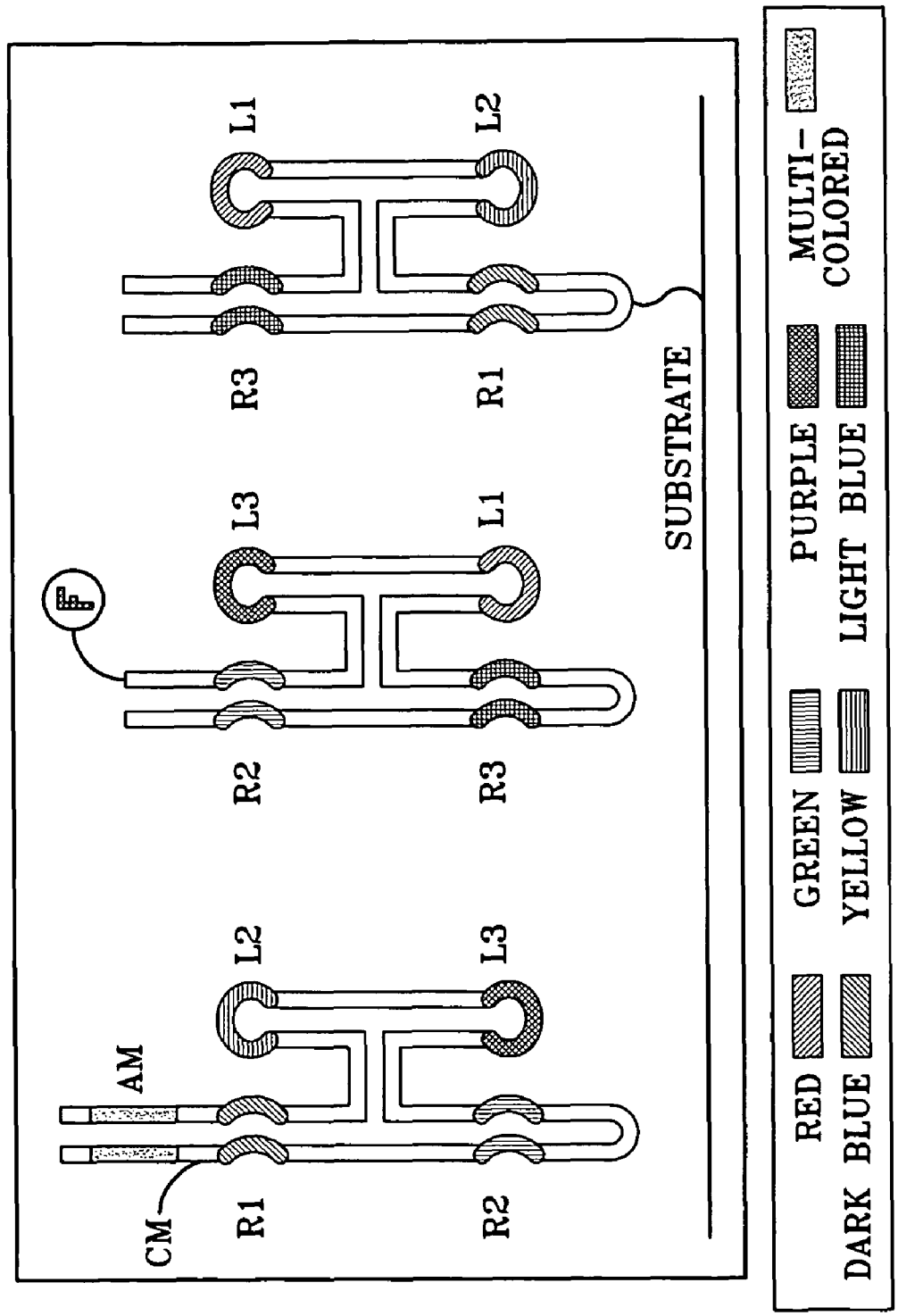
FIG. 17 shows a tectoRNA structure adapted to be used in a FLISA type assay, in accordance with one embodiment of the present invention.

FIG. 17 shows a tectoRNA structure adapted to be used in a FLISA type assay, in accordance with one embodiment of the present invention. FIG. 17 shows an example of a biosensor one may construct using the present invention, that is analogous to an FLISA-type assay. The first tectoRNA binds the analyte at AM. Another tectoRNA is conjugated to a fluorescent reporter molecule (F). A third tectoRNA is immobilized on the surface of the device. In the presence of analyte assembly occurs and excess fluorescently labeled tectoRNA can be washed off prior to detection.

The first and second tectoRNA molecules are free in solution. In the presence of the analyte, they bind to the immobilized tectoRNA; then the well is washed to remove unbound molecules and finally the surface bound fluorescence is measured. This format can be used with many different analytes as the surface bound tectoRNA does not contain the aptamer.
Platform for Systematic Discovery of New RNA Loop-Receptor Interactions for tectoRNA Development.

Figure 18:
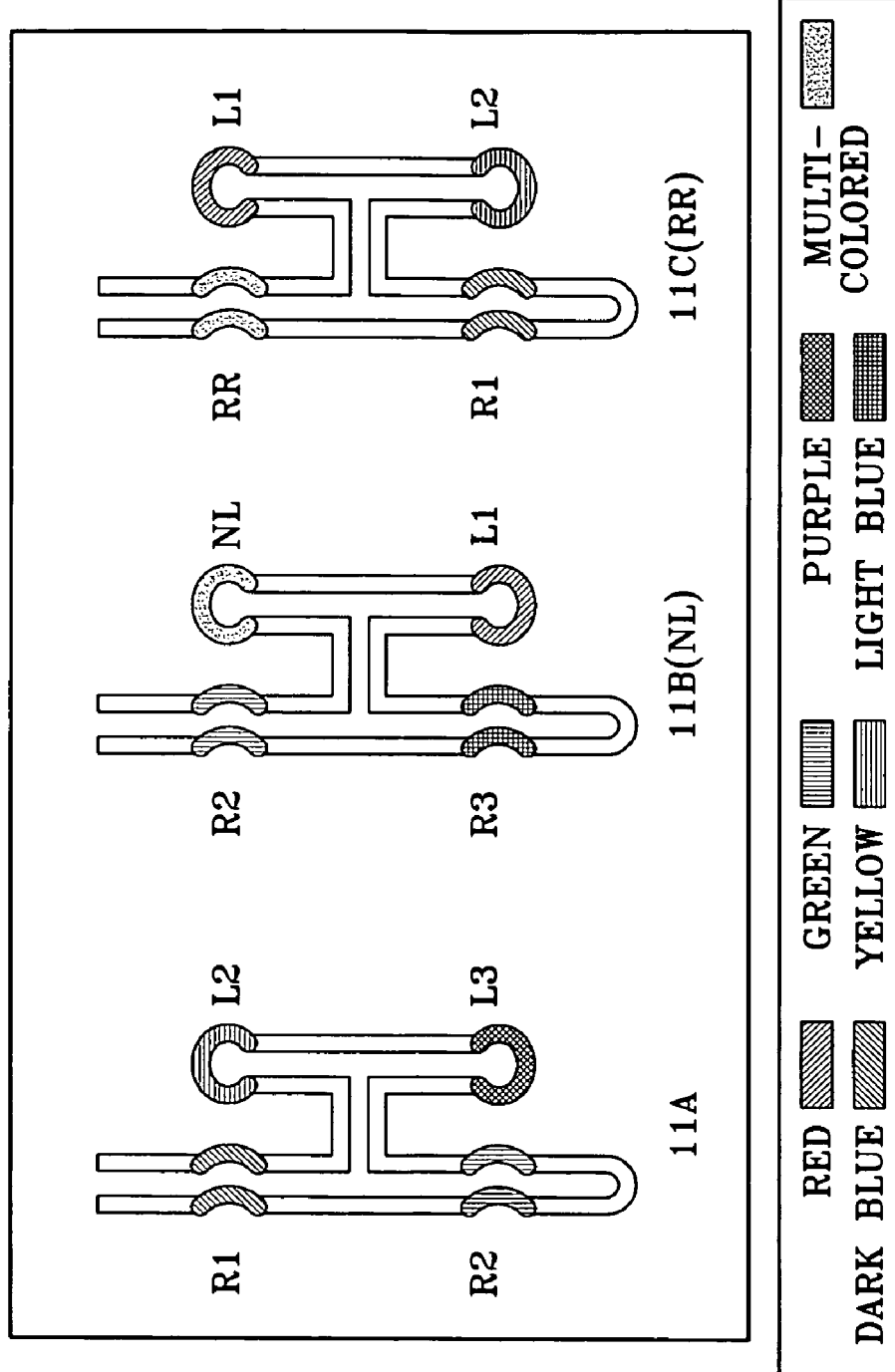
FIG. 18 shows a tectoRNA structure that may be used as a platform for selecting loop-receptors (RR) for new loops, orthogonal to existing loop receptors, in accordance with one embodiment of the present invention.

The 11A/11B/11C(3) trimer system provides a platform for systematic in vitro selection and evolution (SELEX) of orthogonal RNA loop-receptor interaction motifs to complement and extend the set of existing motifs already available for tectoRNA. Molecules designed to carry out this selection are shown in FIG. 18. The "New Loop" (NL) for which a receptor is to be selected is substituted for L3 in molecule 11B(NL). The corresponding receptor region of molecule 11C is randomized to create a library of RNA molecules from which to select molecules that bind to 11B(NL). Positive selection involves mixing the 11C(RR) combinatorial library with 11A and 11B(NL) in the presence of $Mg^{2+}$ ions and running native electrophoresis gels to obtain trimer complexes. Molecules not capable of associating cooperatively with 11A and 11B(NL) to form trimers will run faster on the gel and will be eliminated. Both positive and negative selection is possible with this system, allowing one to obtain truly orthogonal loop-receptor pairs. For example, to ensure that the selected receptors do not bind to L3, the combinatorial library 11C(RR) is subjected to a round of negative selection to eliminate molecules that form trimer complexes when 11B is substituted in place of 11B(NL). This is done by running native gels and selecting molecules that do not associate with 11B to form dimers or with 11A and 11B to form trimers.

FIG. 18 shows a tectoRNA platform for selecting loop-receptors (RR) for new loops, orthogonal to existing loop receptors.
Platform for Systematic Discovery of Aptamers for Molecular Targets of Interest The cooperative 11A/11B/11C system will also serve as a general platform for discovery of new aptamers for molecular targets of interest, including small molecules, proteins, or nucleic acids of environmental, toxicological, or medical interest. Moreover, it can serve as a platform for optimizing known aptamers to increase affinity and sensitivity in the concentration range of interest. A typical scheme for selection or refinement of an existing aptamer to function optimally within the tectoRNA context is shown in FIG. 19.

Figure 19:
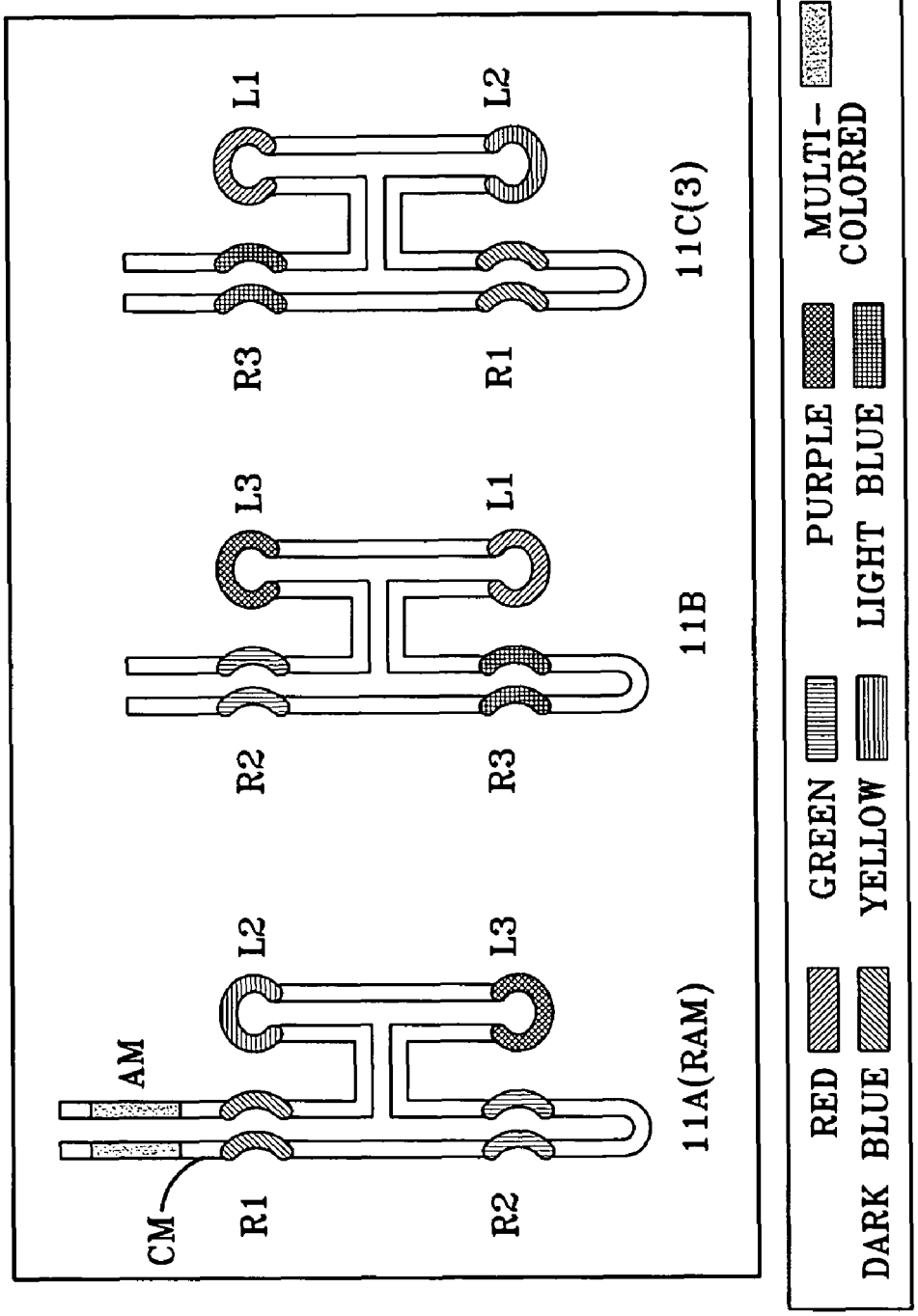
FIG. 19 shows a tectoRNA structure that may be used as a platform for selecting cooperative aptamers for molecular targets of choice, in accordance with one embodiment of the present invention.

Monomer 11A(RA) in FIG. 19 includes module RAM which is coupled to loop receptor R2 by a short communication module. RAM is a randomized region for selecting new aptamers for a target of interest or for optimizing a known aptamer by randomizing at a selected level. The selection procedure may use native gel electrophoresis to select molecules in the library, 11A(RAM), that bind to 11B and 11C(3) to form trimer cooperative complexes at low (submicromolar) RNA concentrations in the presence of the analyte. Negative selection may be carried out to eliminate molecules in the library that form trimers in the absence of the analyte, or that do not bind the analyte in the desired concentration range. These experiments may be used to prove the concept of this aspect of the invention. However, one may also determine the performance of well-characterized aptamers, such as the malachite green aptamer, in the tectoRNA context and then characterizing the thermodynamics of the interaction.

FIG. 19 shows a tectoRNA platform for selecting cooperative aptamers for molecular targets of choice. RAM indicates the positions randomized to select for aptamers coupled to the loop-receptor R1.

In vitro selection may be applied to the B tectoRNA unit to improve the sensitivity to analyte binding. This system can be used as a platform for evolving even better analyte-responsive polymerization systems.
Expandable tectoRNA Molecules for Application to Microcantilever-Based Biosensors Microfabricated silicon cantilevers coated with gold have been developed recently and used to transduce receptor-ligand binding and DNA hybridization into a direct nanomechanical response—cantilever bending—that can be measured by simple optical detection of the nanomechanical bending of the cantilever (Fritz et al. 2000). Such devices are also described in U.S. Pat. No. 6,866,819, which is hereby incorporated herein by reference.

This nanoactuation mechanism has important advantages, because cantilevers are microfabricated by standard low-cost silicon technology and, by virtue of the size achievable, are extremely sensitive to detect biological interactions. An important advantage of biosensors based on miniaturized silicon cantilevers is that no external probes or labeling is required. Biospecific interactions occur between a receptor immobilized on one side of a cantilever and a ligand in solution. This can cause the cantilever to bend, which is detected optically. Recently, a microarray of cantilevers was reported which was used to detect multiple unlabeled biomolecules simultaneously at nanomolar concentrations within minutes (McKendry et al. 2002). Experiments with protein A-immunoglobulin interactions as well as DNA demonstrate the wide-ranging applicability of nanomechanical transduction to detect biomolecular recognition. DNA hybridization experiments showed that the origin of cantilever motion lies in the interplay between changes in configurational entropy and intermolecular energetics induced by specific biomolecular interactions. By controlling entropy change during DNA hybridization, the direction of cantilever motion can be manipulated (Wu et al. 2001). These studies have suggested that the cantilever motion originates from predominantly steric hindrance effects and depends on the concentration of DNA molecules in solution.

The potential of tectoRNA for developing effective biosensors using microcantilever technology is therefore clear. For instance, expandable tectoRNA complexes have the potential to produce large changes in surface energy and thus sensitively to induce cantilever bending. A tectoRNA monomer that can form either a trimer or a larger (~hexamer) expanded complex can be derivatized with a thiol group on one end to attach it to the gold surface of a microcantilever. It is complexed with unfunctionalized monomer units to form a trimer complex and allowed to react with the surface in the presence of divalent cations, thus coating the surface with trimer complexes. After reaction, the surface is washed with EDTA solution to dissociate the trimers leaving the monomer unit on the surface. The microcantilever is next treated with a solution containing tectoRNA subunits that can associate with the surface-bound RNA subunit to form expanded complexes (e.g. hexamers). By introducing a specific aptamer module into one of these subunits, assembly can be made to depend on the presence of the analyte of choice. Formation of the expanded complexes in place of the trimers on the surface produces crowding on the cantilever surface and causes cantilever bending which can be detected—thus transducing RNA aptamer binding of analyte without labeling. As described, the system is modular and can be used with different analytes by using different dissociable aptamer binding tectoRNA. Accordingly, the system may be adapted: (1) To create defined expandable RNA complexes using combinations of compensated and uncompensated interactions, as described above; and (2) To introduce aptamer modules coupled with communication modules to RNA association modules, as described above, to produce tectoRNA that form expanded complexes in response to the presence of an analyte. For this purpose one may use a well-characterized aptamer such as the malachite green aptamer.

By using aptamers in accordance with tectoRNA constructs of the present invention, the present invention may also include modified microcantilever surfaces to create novel, modular, high-throughput, real-time biosensors.

RNA Preparation and Manipulations

RNA may be synthesized by standard techniques using run-off transcription of DNA templates using T7 RNA Polymerase. DNA templates are prepared by PCR amplification of synthetic oligonucleotides which may be designed using a computer program, such as the web application developed for automating the process of converting RNA sequences to DNA template and primer sequences (currently available at http://personal.bgsu.edu/~jstomba/index.html). RNA is purified by denaturing gel electrophoresis and radiolabeled with 32P-pCp on the 3'-end or by kinasing on the 5'-end. RNA is routinely purified using preparative denaturing electrophoresis and electroelution followed by alcohol precipitation.

Fluorescence Measurements

Conformational changes induced in tectoRNA monomers upon assembly may be studied using static and time-resolved FRET and other fluorescence techniques. FRET and other fluorescence measurements are carried out using the Edinburgh Instruments FUFS 900. Fluorimeter. The instrument is equipped with time-correlated single photon counting and provides a dynamic range of 100,000:1. It is equipped with a 450 watt Xenon lamp.

TectoRNA Molecular Modeling and Physical Models

Currently, tectoRNA constructs of the present invention may be modeled using computer models assembled manually using software such as Swiss PDB Viewer to manipulate and dock motifs. MATLAB programs may be written to automate the tedious aspects of model building such as the insertion of helical struts, optimal positioning of overlapping helical segments (to correctly position modular motifs) and renumbering of nucleotides at intermediate stages of modeling. The new programs will draw on MATLAB code we have written to identify and extract RNA motifs and non-Watson-Crick basepairs from crystal structures. The computer models may be converted to physical models using rapid prototyping. Additional models for pairs of interacting tectoRNAs, including the 4WJ, for all feasible variations of distances (in basepairs) between the interacting loop and receptor motifs and the 4WJ may be prepared, to assist in the interpretation of experiments.

Analytical Methods and Apparatus

As can be appreciated from the forgoing description, the self-assembling RNA complexes of the present invention may be applied advantageously to analytical methods and apparatus as summarized herein.

The self-assembling RNA may be constructed using analyte specific aptamers that allow one to detect the presence of one or more analytes that react with discretion with the incorporated aptamer, allowing the self-assembling RNA only when the analyte(s) combine with monomeric unit(s) having analyte-specific aptamers. This provides a scheme by which one or more analytes may be detected from a common solution if desired.

For instance, the self-assembly of RNA complexes can be detected using silicon cantilever devices whose surfaces measurably change upon the formation of an RNA complex thereupon.

REFERENCES

Ball, P. (2002). "Natural Strategies for the Molecular Engineer." *Nanotechnology* 13: R15-R28.

Cate, J. H., A. R. Gooding, E. Podell, K. Zhou, B. L. Golden, C. E. Kundrot, T. R. Cech and J. A. Doudna (1996). "Crystal structure of a group I ribozyme domain: principles of RNA packing." *Science* 273(5282): 1678-85.

Cate, J. H., A. R. Gooding, E. Podell, K. Zhou, B. L. Golden, A. A. Szewczak, C. E. Kundrot, T. R. Cech and J. A. Doudna (1996). "RNA tertiary structure mediation by adenosine platforms." *Science* 273(5282): 1696-9.

Costa, M. and F. Michel (1997). "Rules for RNA recognition of GNRA tetraloops deduced by in vitro selection: comparison with in vivo evolution." *Embo J* 16(11): 3289-302.

Emilsson, G. M. and R. R. Breaker (2002). "Deoxyribozymes: new activities and new applications." *Cell Mol Life Sci* 59(4): 596-607.

Ennifar, E., P. Walter, B. Ehresmann, C. Ehresmann and P. Dumas (2001). "Crystal structures of coaxially stacked kissing complexes of the HIV-1 RNA dimerization initiation site." *Nat Struct Biol* 8(12): 1064-8.

Fritz, J., M. K. Bailer, H. P. Lang, H. Rothuizen, P. Vettiger, E. Meyer, H. Guntherodt, C. Gerber and J. K. Gimzewski (2000). "Translating biomolecular recognition into nanomechanics." *Science* 288(5464): 316-8.

Fu, T. J. and N. C. Seeman (1993). "DNA double-crossover molecules." *Biochemistry* 32(13): 3211-20.

Goodsell, D. S. and A. J. Olson (2000). "Structural symmetry and protein function." *Annu Rev Biophys Biomol Struct* 29: 105-53.

Hermann, T. (2000). "Strategies for the Design of Drugs Targeting RNA and RNA-Protein Complexes." *Angew Chem Int Ed Engl* 39(11): 1890-1904.

Hofacker, I. L. (2003). "Vienna RNA secondary structure server." *Nucleic Acids Res* 31(13): 3429-31.

Hohng, S., T. J. Wilson, E. Tan, R. M. Clegg, D. M. Lilley and T. Ha (2004). "Conformational flexibility of four-way junctions in RNA." *J Mol Biol* 336(1): 69-79.

Jaeger, L. and N. B. Leontis (2000). "Tecto-RNA: One-Dimensional Self-Assembly through Tertiary Interactions This work was carried out in Strasbourg with the support of grants to N. B. L. from the NIH (1R15 GM55898) and the NIH Fogarty Institute (1-F06-TW02251-01) and the support of the CNRS to L. J. The authors wish to thank Eric Westhof for his support and encouragement of this work." *Angew Chem Int Ed Engl* 39(14): 2521-2524.

Jaeger, L., E. Westhof and N. B. Leontis (2001). "TectoRNA: modular assembly units for the construction of RNA nano-objects." *Nucleic Acids Res* 29(2): 455-63.

Kertsburg, A. and G. A. Soukup (2002). "A versatile communication module for controlling RNA folding and catalysis." *Nucleic Acids Res* 30(21): 4599-606.

Klostermeier, D. and D. P. Millar (2002). "Energetics of hydrogen bond networks in RNA: hydrogen bonds surrounding G+1 and U42 are the major determinants for the tertiary structure stability of the hairpin ribozyme." *Biochemistry* 41(48): 14095-102.

Liao, S. and N. C. Seeman (2004). "Translation of DNA signals into polymer assembly instructions." *Science* 306 (5704): 2072-4.

Mao, C., W. Sun, Z. Shen and N. C. Seeman (1999). "A nanomechanical device based on the B-Z transition of DNA." *Nature* 397(6715): 144-6.

McKendry, R., J. Zhang, Y. Arntz, T. Strunz, M. Hegner, H. P. Lang, M. K. Bailer, U. Certa, E. Meyer, H. J. Guntherodt and C. Gerber (2002). "Multiple label-free biodetection and quantitative DNA-binding assays on a nanomechanical cantilever array." *Proc Natl Acad Sci USA* 99(15): 9783-8.

Nutiu, R. and Y. Li (2004). "Structure-switching signaling aptamers: transducing molecular recognition into fluorescence signaling." *Chemistry* 10(8): 1868-76.

Roco, M. C. (2003). "Nanotechnology: convergence with modern biology and medicine."*Curr Opin Biotechnol* 14(3): 337-46.

Seeman, N. C. (2003). "Biochemistry and structural DNA nanotechnology: an evolving symbiotic relationship." *Biochemistry* 42(24): 7259-69.

Seeman, N. C. (2003). "DNA in a material world." *Nature* 421(6921): 427-31.

Stojanovic, M. N. and D. M. Kolpashchikov (2004). "Modular aptameric sensors." *J Am Chem Soc* 126(30): 9266-70.

Whitesides, G. M. and M. Boncheva (2002). "Beyond molecules: self-assembly of mesoscopic and macroscopic components." *Proc Natl Acad Sci USA* 99(8): 4769-74.

Winfree, E., F. Liu, L. A. Wenzler and N. C. Seeman (1998). "Design and self-assembly of two-dimensional DNA crystals." *Nature* 394(6693): 539-44.

Winkler, W. C. and R. R. Breaker (2003). "Genetic control by metabolite-binding riboswitches." *Chembiochem* 4(10): 1024-32.

Wu, G., H. Ji, K. Hansen, T. Thundat, R. Datar, R. Cote, M. F. Hagan, A. K. Chakraborty and A. Majumdar (2001). "Origin of nanomechanical cantilever motion generated from biomolecular interactions." *Proc Natl Acad Sci USA* 98(4): 1560-4.

Yan, H., X. Zhang, Z. Shen and N. C. Seeman (2002). "A robust DNA mechanical device controlled by hybridization topology." *Nature* 415(6867): 62-5.

Zhang, X., H. Yan, Z. Shen and N. C. Seeman (2002). "Paranemic cohesion of topologically-closed DNA molecules." *J Am Chem Soc* 124(44): 12940-1.

The foregoing references are hereby incorporated herein by reference.

What is claimed is:

1. An RNA complex comprising:
   at least three monomeric units, each said monomeric unit comprising RNA having a first double helical domain having a first binding site and a second binding site, said first double helical domain connected by a four-way junction to a second double helical domain having a first binding site and a second binding site, such that said first double helical domain and said second double helical domain are held in position with respect to one another; such that said at least three monomeric units are adapted to self-assemble by respective first binding sites interacting with first binding sites of respective adjacent monomeric units, and respective second binding sites interacting with second binding sites of respective adjacent monomeric units to form pairs of cognate interactions and so as to form said RNA complex in a circular closed complex, wherein said first double helical domain and said second double helical domain are substantially parallel, and wherein said first double helical domain and said second double helical domain are held in position with respect to one another by said four-way junction, and wherein the positions of said first binding sites and said second binding sites are maintained such that said first binding sites and said second binding sites are spatially compatible in only one possible orientation of respective adjacent monomeric units.

2. An RNA complex according to claim 1 wherein at least one of said first binding sites is incompatible with at least one of said at least one second binding sites, and said second binding site being incompatible with at least one said first binding site.

3. An RNA complex according to claim 1 wherein said first and second binding sites bind to one another through non-Watson-Crick interactions.

4. An RNA complex according to claim 1 wherein said RNA complex is selected from the group consisting of trimers, tetramers, pentamers, hexamers, heptamers or octamers.

5. An RNA complex according to claim 1 wherein said first binding sites of respective adjacent monomeric units are adapted to bind to one another and are not adapted to bind to said second binding sites of respective adjacent monomeric units, and said second binding sites of respective adjacent monomeric units are adapted to bind to one another and are not adapted to bind to said first binding sites of respective adjacent monomeric units.

6. A method of making a self-assembled RNA complex comprising the steps:
   (a) placing in solution at least three monomeric units comprising RNA, each said monomeric unit comprising RNA having a first double helical domain having a first binding site and a second binding site, said first double helical domain connected by a four-way junction to a second double helical domain having a first binding site and a second binding site, such that said first double helical domain and said second double helical domain are held in position with respect to one another, wherein said first double helical domain and said second double helical domain are substantially parallel, and wherein the positions of said first binding sites and said second binding sites are maintained such that said first binding sites and said second binding sites are spatially compatible in only one possible orientation of respective adjacent monomeric units.
   (b) allowing said at least three monomeric units to react such that said at least three monomeric units self-assemble by respective first binding sites interacting with first binding sites of respective adjacent monomeric units, and respective second binding sites interacting with second binding sites of respective adjacent monomeric units, to form pairs of cognate interactions and so as to form said RNA complex in a circular closed complex.

7. The method according to claim 6 wherein at least one of said double helical domains of said monomeric units comprises a fluorescent moiety.

8. An RNA complex comprising:
   at least three monomeric units, each said monomeric unit comprising RNA having a first double helical domain having a first binding site and a second binding site, said first double helical domain connected by a four-way junction to a second double helical domain having a first binding site and a second binding site, such that said first double helical domain and said second double helical domain are held in position with respect to one another and are substantially parallel; such that said at least three monomeric units are adapted to self-assemble by respective first binding sites interacting with first binding sites of respective adjacent monomeric units, and respective second binding sites interacting with second binding sites of respective adjacent monomeric units to form pairs of cognate interactions and so as to form said RNA complex in a circular closed complex and wherein the positions of said first binding sites and said second binding sites are maintained such that said first binding sites and said second binding sites are spatially compatible in only one possible orientation of respective adjacent monomeric units, wherein at least one of said first binding sites is incompatible with at least one of said second binding sites, and said second binding site being incompatible with said first binding site, and wherein said first and second binding sites bind to one another through non-Watson-Crick interactions.

9. An RNA complex according to claim 1 wherein at least one of said double helical domains of said monomeric units comprises a fluorescent moiety.

10. An RNA complex according to claim 8 wherein said RNA complex is selected from the group consisting of trimers, tetramers, pentamers, hexamers, heptamers or octamers.

11. An RNA complex according to claim 8 wherein at least one of said double helical domains of said monomeric units comprises a fluorescent moiety.

* * * * *